(12) United States Patent
Pfahl et al.

(10) Patent No.: US 7,098,310 B1
(45) Date of Patent: Aug. 29, 2006

(54) HETERODIMERS OF RETINOID X RECEPTORS (RXRS) AND OTHER STEROID HORMONE RECEPTORS

(75) Inventors: Magnus Pfahl, Solana Beach, CA (US); Xiao-kun Zhang, La Jolla, CA (US)

(73) Assignee: Ligand Pharmaceuticals, San Diego, CA (US)

( * ) Notice: Subject to any disclaimer, the term of this patent is extended or adjusted under 35 U.S.C. 154(b) by 0 days.

(21) Appl. No.: 07/814,871

(22) Filed: Dec. 24, 1991

(51) Int. Cl.
*C07K 14/435* (2006.01)
*G01N 33/78* (2006.01)

(52) U.S. Cl. .............................. 530/350; 435/7.1; 514/2

(58) Field of Classification Search ................. 435/2.1, 435/501; 530/350, 827, 399, 402; 514/2
See application file for complete search history.

(56) References Cited

U.S. PATENT DOCUMENTS 5,654,137 A * 8/1997 Astrom et al.

OTHER PUBLICATIONS

Hamada, K. et al., "H–2RIIBP, a member of the nuclear hormone receptor superfamily that binds to both the regulatory element of major histocompatibility class I genes and the estrogen response element," *Proc. Natl. Acad. Sci. U.S.A.* 86:8289–8293 (1989).
Yu, V.C., et al (1991) Cell 67: 1251–66.*
Mangelsdorf, D.J., et al (1990) Nature 345: 224–29.*
Glass, C.K., et al (1989) Cell 59: 697–708.*
Glass, C.K., et al (1990) Cell 63: 729–38.*
Darling, D.S., et al. (1991) Mol. Endocrinol. 5: 73–84.*

* cited by examiner

*Primary Examiner*—Robert Landsman
(74) *Attorney, Agent, or Firm*—McDermott Will & Emery LLP

(57) ABSTRACT

This invention provides a purified heterodimer comprising an RXR and a hormone receptor. The invention also provides a method of screening ligands for their effect on the activity of an RXR-containing hormone receptor heterodimer comprising combining the heterodimer with the ligand and determining the effect on activity. Also provided is a method of amplifying the activity of a hormone receptor comprising forming a heterodimer with another hormone receptor.

9 Claims, 22 Drawing Sheets

HETERODIMERS OF RETINOID X RECEPTORS (RXRS) AND OTHER STEROID HORMONE RECEPTORS

This invention was made with government support under Grant Numbers DK35083 and CA50676 from the National Institutes of Health. The U.S. Government has certain rights in this invention.

Full citations for referenced publications may be found at the end of the specification immediately preceding the claims. The disclosures of these publications in their entireties are hereby incorporated by reference into this application in order to more fully describe the state of the art to which this invention pertains.

BACKGROUND OF THE INVENTION

Thyroid hormones as well as retinoic acid (RA) function through multiple nuclear receptors that belong to the steroid/thyroid hormone receptor superfamily (reviewed by Evans 1988; Green and Chambon, 1988). The thyroid hormone receptors (TR) are encoded by two genes (Weinberger et al., 1986; Jansson et al., 1983), referred to as TRα and TRβ from which multiple isoforms are generated (Benbrook and Pfahl, 1987; Nakai et al., 1988; Mitsuhashi et al., 1988; Lazar et al., 1989; Koenig et al., 1989; Sakurai et al., 1989; Hodin et al., 1989). The known TRα subtypes are generated by alternative mRNA splicing yielding several isoforms with distinct carboxyterminal regions (Sap et al., 1986; Benbrook and Pfahl, 1987; Thompson et al., 1987; Mitsuhashi et al, 1988; Nakai et al., 1988). Only one of these isoforms, TRα-1, is a classical ligand dependent transcriptional activator, while for the other splicing variants (TRα-2 and TRα-2V) a function as transcriptional activator could not be demonstrated (Mitsuhashi et al, 1988; Lazar et al., 1989; Koenig et al., 1989; Schueler et al., 1990; Hermann et al., 1991). Although TRα-2 has been shown to exhibit weak repressor activity (Lazar et al., 1989; Koenig et al., 1989; Hermann et al., 1991), the biological functions of the carboxyterminal TRα variants are not well understood. Two TRβ forms have been described (Weinberger et al., 1986; Hodin et al., 1989) that differ in their amino terminal regions and both are transcriptional activators. Besides their classical roles as ligand dependent enhancer proteins, TRα-1 and TRβ-1 function as transcriptional repressors and/or silencer proteins in the absence of ligand (Graupner et al., 1989; Damm et al., 1989; Zhang et al., 1991b; Brent et al., 1989; Graupner et al., 1991; Baniahmad et al., 1990).

Retinoic acid receptors (RAR) are encoded by three genes RARα, β, and γ(Petkovich et al., 1987; Giguere et al., 1987; Benbrook et al., 1988; Krust et al., 1989) from which multiple isoforms that differ in their amino terminal regions, are generated by a combination of alternative promoter usage and alternative splicing (Zelent et al., 1991; Lehmann et al., 1991; Leroy et al., 1991). All RAR isoforms can antagonize each other's activity (Husmann et al., 1991). A second type of RA receptor was more recently described that is only activated by high concentrations of RA and does not show significant homology in its ligand binding domain with RAR but has significant homology in its DNA binding domain (Mangelsdorf et al., 1990). It has been proposed that this receptor may be activated by an unknown RA metabolite derivative (Mangelsdorf et al., 1990) and it has been designated retinoid x receptor (RXRα). This receptor is highly homologous to a previously isolated orphan receptor H-2 RIIBP (Hamada et al., 1989) now usually referred to as RXRβ.

TRs as well as the retinoid receptors are believed to function as dimeric or multimeric proteins since they recognize and bind specifically to dimeric or multimeric response elements, that are either direct repeats or palindromic repeats. Certain response elements like the palindromic TRE, are activated by all three types of receptors, TRs, RARs, and RXRs (Umesono et al., 1988; Graupner et al., 1989; Mangelsdorf et al., 1990) while other response elements are receptor specific (Hoffmann et al., 1990; Umesono et al., 1991; Naar et al., 1991). A direct repeat of the sequence TGACCT can function as a specific response element for TRs, RARs and vitamin D receptors depending on whether the repeats are separated by 4, 5 or 3 spacer nucleotides, respectively (Umesono et al., 1991). However, spacing between half-sites of response elements does not solely determine receptor specificity (Naar et al., 1991; our unpublished results).

Although a large set of data appears to suggest that TRs and RARs function as homodimers, there exists no convincing experimental evidence yet that these proteins interact with their responsive elements in vivo or in vitro specifically as homodimers. To the contrary, an increasing volume of data suggests that TRs as well as RARs require accessory nuclear proteins for efficient DNA binding (Lazar and Berrodin, 1990; Glass et al., 1990; Murray and Towle, 1989; Burnside et al., 1990; Zhang et al., 1991a), consistent with recent data from others (Forman and Samuels, 1991). Deletion of a portion of the TRα carboxyterminal region appears to increase DNA binding and greatly enhances dimerization and/or oligomerization, suggesting that one dimerization domain of TRα is located in the "DNA binding domain" (DBD). This concept is supported by structural data on the glucocorticoid (GR) (Härd et al., 1990; Luisi et al., 1991) and estrogen (ER) receptors (Schwabe et al., 1990). A second dimerization/oligomerization domain was found to be located in the "ligand binding domain" (LBD), a region that has been suggested to form a leucine zipper type structure (Forman et al., 1989). Part of the carboxyterminal region appears to inhibit the dimerization function of TRα such that homodimers with a palindromic TRE are not efficiently formed (Zhang et al., 1991a). Enhancement of DNA binding and the formation of a slow electrophoretic mobility complex required the presence of a protein present in nuclear extracts from a number of cell lines including F9 cells, CV-1 cells, and GC cells (Zhang et al., 1991a).

The nature of this protein could not be determined, however it is reasonable to hypothesize that this protein(s) and/or the proteins that interact with TRs and RARs, as described by others (Lazar and Berrodin, 1990; Glass et al., 1990; Murray and Towle, 1989; Burnside et al., 1990; Rosen et al., 1991) are important components for these nuclear receptors that regulate their activity. Whether the protein(s) are members of the nuclear receptor family is not yet known, however we present data in this publication that one of the retinoid receptors, RXRα, strongly enhances binding of TRs and RARs to several response elements. Studies of the enhanced and upshifted TR or RAR complexes by antibodies and receptor mutants demonstrate that RXRα can form a heterodimer with TRs and RARs. The interaction can occur in the absence of DNA and requires both DNA and ligand binding domains of RXRα and the ligand binding domain of TRs or RARS. In cotransfection experiments, RXRα greatly enhances TR and RAR transcriptional activation activity at retinoic acid concentrations where RXRα itself is not significantly activated. Our data suggest that RXRα belongs to a novel class of nuclear receptors that we would like to term "booster receptors" (B-receptors) that at low ligand concentrations greatly enhance the activity of other receptors by heterodimer formation while, when by themselves, can not dimerize efficiently and have only low affinity for their ligands.

SUMMARY OF THE INVENTION

This invention provides a purified heterodimer comprising an RXR and a hormone receptor. The invention also provides a method of screening ligands for their effect on the activity of an RXR-containing hormone receptor heterodimer comprising combining the heterodimer with the ligand and determining the effect on activity. Also provided is a method of amplifying the activity of a hormone receptor comprising forming a heterodimer with another hormone receptor.

Figure 1A:
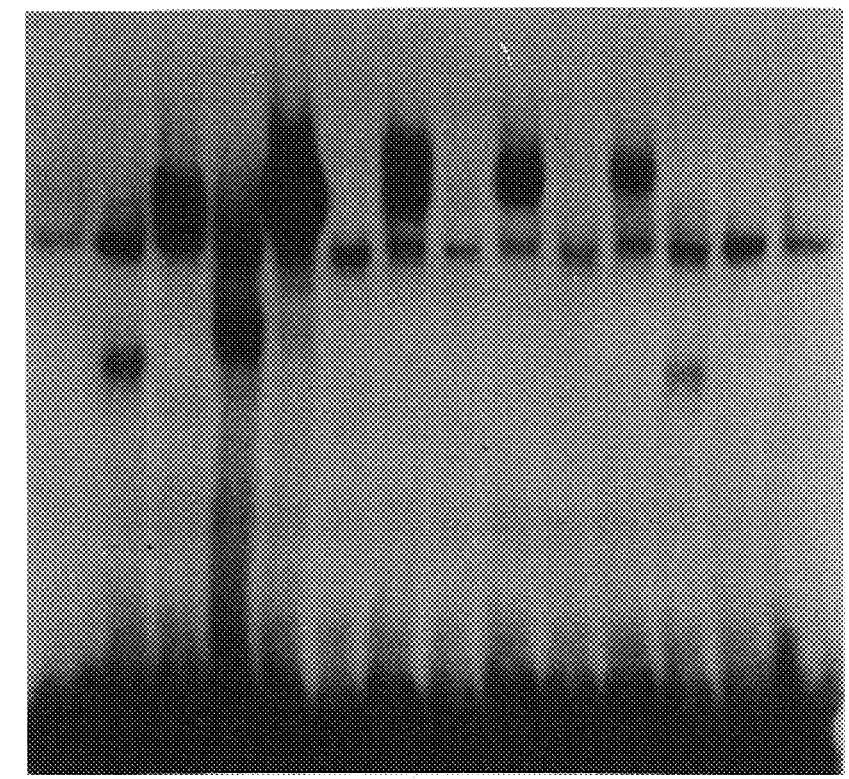
FIG. 1. Enhancement of TRα and RAR DNA binding by RXRα

(a) In vitro synthesized TRα, TRβ, RARα, RARβ, RARγ and TRα2 receptor proteins were preincubated either with (+) or without (−) equal amount of in vitro synthesized RXRα protein at room temperature for 10 minutes. Following this preincubation, the reaction mixtures were incubated with $^{32}$p-labelled palindromic TRE (for sequence see FIG. 2a) and analyzed by gel retardation assay as described in Experimental Procedures. Lane 1 represents binding of unprogrammed reticulocyte lysate. The nonspecific band observed with unprogrammed reticulocyte lysate is indicated by the open triangle. Complexes migrating below or above the nonspecific band are the specific comlexes of TRs in the absence of RXRα and the complexes formed by TRs and RARs in the presence of RXRα. As a control, equal amounts of TRα and RARα proteins were also mixed and incubated with labelled TRE.

(b) Effect of estrogen receptor. To analyze whether ER could also enhance TRα binding to the TRE, or whether RXRα would enhance ER binding to the ERE, equal amounts of in vitro synthesized ER protein were incubated with TRα or RXRα proteins and the reaction mixtures were analyzed by gel retardation using either $^{32}$p-labelled palindromic TRE or palindromic ERE as indicated. Control represents the binding of the unprogrammed reticulocyte to ERE. The nonspecific bands observed with unprogrammed lysate are indicated by the open triangles.

(c) Effect of CV-1 cell extract on TRα DNA binding. Cell extract was prepared from CV-1 cells as described in the Experimental Procedures and the different amounts of cell extract (in microgram) were incubated either with in vitro synthesized TRα protein or the same volume of unprogrammed reticulocyte lysate. The reaction mixtures were then analyzed by gel retardation using $^{32}$p-labelled palindromic TRE. Open triangle, solid arrow, and solid diamond indicate the nonspecific binding of the reticulocyte lysate, specific TRα binding, and the upshifted TRα complex, respectively.

(d) Interaction of RXRα with TR and RAR is ligand independent. The effect of T$_3$ (10$^{-7}$ M) or RA (10$^{-7}$ M) on the interaction between RXRα and TRα or RARα was analyzed by gel retardation as described in FIG. 1a. Open triangle indicates the nonspecific binding of the unprogrammed reticulocyte lysate.

FIG. 2. RXRα forms a complex with TRs and RARS.

(a) Effect of anti-FLAG-RXRα on the slow migrating complex. In vitro synthesized FLAG-RXRα (F-RXRα) protein was incubated with in vitro synthesized TRα, TRβ, RARα RARβ and RARγ as indicated, in the presence of anti-FLAG antibody (α-FLAG). After incubation at room temperature for 45 minutes, the effect of antibody on slow migrating complexes was analyzed by gel retardation using $^{32}$-labelled palindromic TRE as a probe. As a control, receptor mixtures were also incubated with preimmune serum (NI). The effect of anti-FLAG antibody on FLAG-RXRα, TRα, TRβ, RARα, RARβ and RARγ was also shown. Empty triangle represents the binding of unprogrammed reticulocyte lysate (lane 1). Solid triangle represents the binding of antibody-shifted FLAG-RXRα protein. Arrow represents the binding of antibody-shifted FLAG-RXRα-TRβ heterodimer.

(b) Effect of anti-FLAG-TRα antibody on binding of the slow migrating complex. In vitro synthesized FLAG-TRα (F-TRα) protein was incubated with in vitro synthesized RXRα protein in the presence or absence of anti-FLAG antibody. The effect of antibody on DNA binding of the slow migrating complex was analyzed as described in FIG. 2a. For control, the receptor mixture was also incubated with preimmune serum (NI). The effect of anti-FLAG antibody on DNA binding of FLAG-RXRα, RXRα, Flag-TRα, and TRα was also analyzed. For comparison, anti-FLAG antibody/FLAG-RXRα-TRα interaction was run on the same gel (lanes 7–10). Open triangle represents the nonspecific binding of the unprogrammed reticulocyte lysate. Solid triangle represents the binding of the antibody-shifted RXRα protein. Arrow indicates the binding of antibody-upshifted FLAG-TRα protein.

(c) Effect of anti-FLAG-RARγ antibody on the slow migrating complex. The assay was carried out as described in FIG. 2b. Open triangle represents the binding of the unprogrammed reticulocyte lysate. Solid triangle indicates the binding of antibody-upshifted FLAG-RXRα protein.

FIG. 3. Interaction of TRα and RXRα on different DNA response sequences.

(a) Sequences of oligonucleotides used for the gel retardation assays. TRE (SEQ ID NO:9) is the perfect palindromic T3/RA response element (Glass et al., 1988; Graupner et al., 1989). TRE/OP (SEQ ID NO:10) is an oligonucleotide consisting of two TRE half-site, (as indicated by the arrows) in opposite orientation separated by 4 bp. βRARE (SEQ ID NO:11) is a RA response element present in the RARβ promoter (Hoffmann et al., 1990). TRE/half (SEQ ID NO:12) is the half-site of TRE. ERE (SEQ ID NO:13) is the perfect palindromic ER response element (Klein- Hitpass et al., 1986). These oligonucleotides were synthesized with appropriate restriction sites at both ends as indicated by the small letters.

(b) Gel retardation analysis of RXRα-TRα interaction using different DNA response elements. Gel retardation assays were carried out essentially as described in FIG. 1a but using different response elements. (−) represents the binding of unprogrammed reticulocyte lysate. Specific binding of TRα to each response element is indicated by the solid arrows. Non specific bands observed with unprogrammed reticulocyte lysate are indicated by open triangles. Binding TRα to βRARE or RXRα to all response elements was not visible under the conditions used. The heterodimer formation (TRα/RXRα) was clearly observed on the TRE, the TRE/OP and the βRARE (as indicated by the diamonds) but not on TRE/half and the ERE.

FIG. 4. Ligand binding domains of TR and RAR are essential for the interaction of RXRα.

(a) Schematic representations of the TRα and c)RARγ deletion mutants. Numbers above the bars indicate the amino acids positions. DNA binding domain (DBD) and the ligand binding domain (LBD) are shown. A leucine-Zipper-like motif (Foreman et al., 1990) in the LBD of the TRα and RARγ containing 9 heptad repeats is indicated by the black bars.

Interaction of RXRα with the TRα and d) RARγ deletion mutants. TR and RAR deletion mutant proteins were synthesized in vitro as described in the Experimental Procedures. Equal amounts of TR and RAR proteins and the mutant proteins were analyzed for their interaction with RXRα using the gel retardation assay with the palindromic TRE as described in FIG. 1a. The nonspecific binding of the unprogrammed reticulocyte lysate is indicated by the open triangles.

Figure 5A:
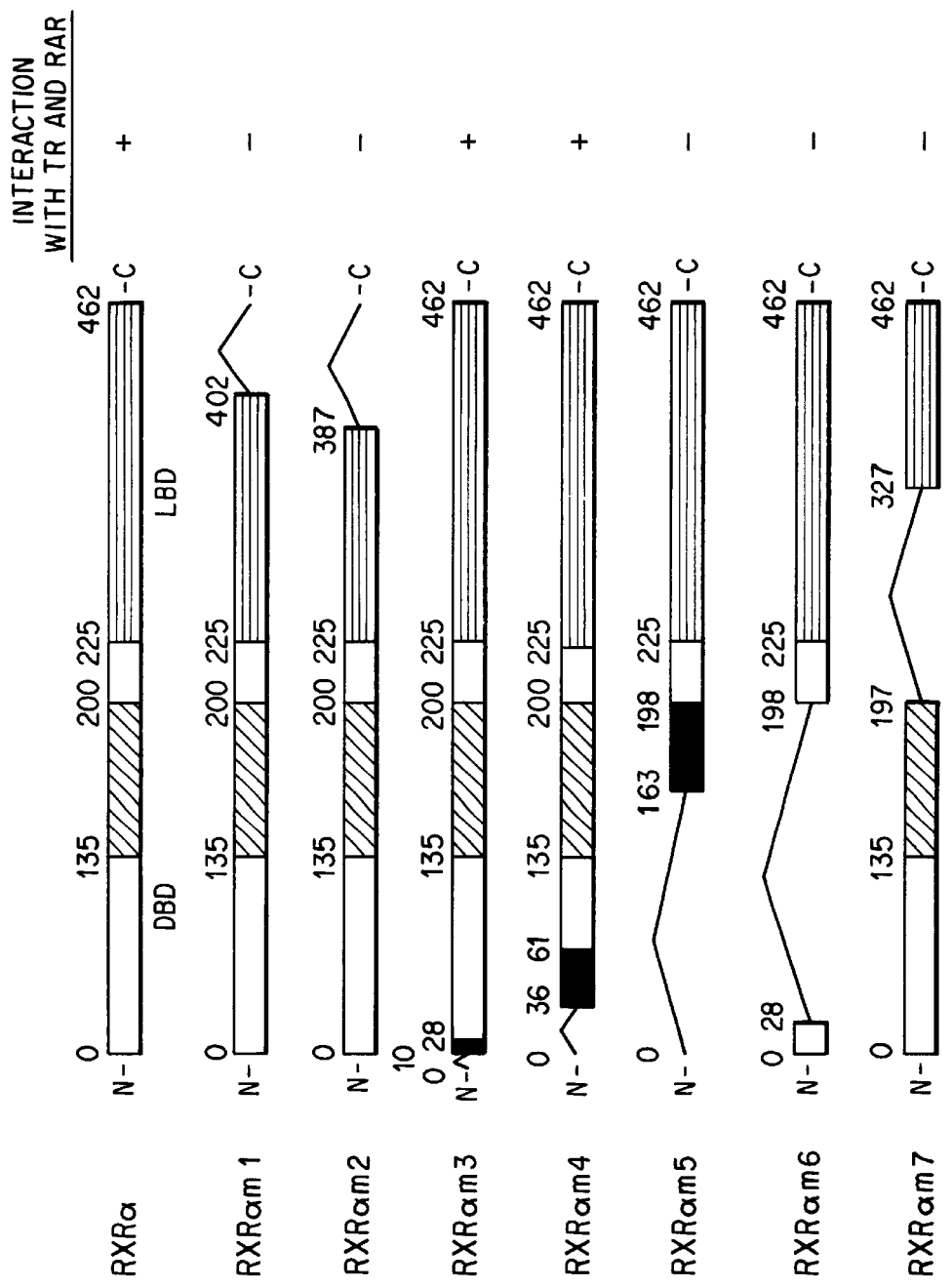

FIG. 5. Both DNA and ligand binding domains of RXRα are required for interaction with TR and RAR.

(a) Schematic representation of the RXRα deletion mutants. RXRα deletion mutants were constructed and proteins were prepared as described in the Experimental Procedures. Numbers above the bars indicate the amino acid positions. DNA binding domain (DBD) and ligand binding domain (LBD) are indicated. Single lines mark the deleted portions of the receptor. Deletion mutants RXRαm3, RXRαm4 and RXRαm5 are truncated cDNA clones of RXRα isolated from screening the human placenta γgt11 cDNA library. These clones were sequenced and show identical nucleotide sequence as the wild type RXRα. The proteins of these cDNA clones were translated in vitro using existing MET codons for amino acid 28, 61 and 198, respectively, as determined by SDS-PAGE. The black bars indicate the untranslated portions of these three mutants.

Interaction of RXRα deletion mutants with b) TRα and c) RARγ. Interaction of RXRα deletion mutants with TRα and RARγ was analyzed by the gel retardation assay essentially as described in FIG. 1a. The first lane represents the binding of the unprogrammed reticulocyte lysate. The nonspecific binding is indicated by the open triangles. The specific binding of TRα migrates faster than the nonspecific band. RARγ by itself shows no visible binding to TRE under the condition used. Arrows indicate the migration positions of complexes formed with RXRαm3 and RXRαm4.

FIG. 6. RXRα enhances the transcriptional activation of RAR.

(a) CV-1 cells were cotransfected with 100 ng of $TRE_2$-CAT and the indicated amounts of the receptor expression vector. Cells were treated with 100 nM RA (■) or no hormone (□), and 24h later assayed for CAT activity. The mean of duplicate cultures is shown.

(b) The TRE-tk-CAT reporter was cotransfected into CV-1 cells with 5 ng RXRα, or 5 ng RARγ, or 5 ng of each receptor expression vector. Cells were treated with indicated concentrations of RA and assayed for CAT activity as described in the Experimental Procedures. The activity of RXRα on the reporter gene in the absence of either hormone was chosen as reference value, and CAT activities were normalized accordingly. The mean of duplicate experiments is shown.

FIG. 7. Induction curves of RXRα in the presence and absence of TRα.

The single palindromic TRE reporter gene (7a) or the double TRE reporter (7b) (100 ng/well) were transfected into CV-1 cells together with 5 ng RXRα, 100 ng reporter gene, 150 ng β-galactosidase plasmid, 25 ng TRα (or no TRα) and pBLUESCRIPT up to 1000 ng. Cells were grown in 24 well plates with the indicated amounts of RA and a constant amount of $10^{-7}$ M $T_3$. CAT activities were corrected for transfection efficiency by β-gal values. As control, reporter constructs were transfected alone, and CAT activities were analyzed after the same hormone treatment as described above. The activity of RXRα on the reporter gene in the absence of either hormone was chosen as reference value, and CAT activities were normalized accordingly. The mean values from 4 to 6 independent transfection experiments as shown. Note that CAT activities elicited by T3 after cotransfection of TRα and RXRα or TRα alone correspond to 5-fold induction from the single TRE and 10–15-fold induction from the double TRE, respectively.

Figure 8A:
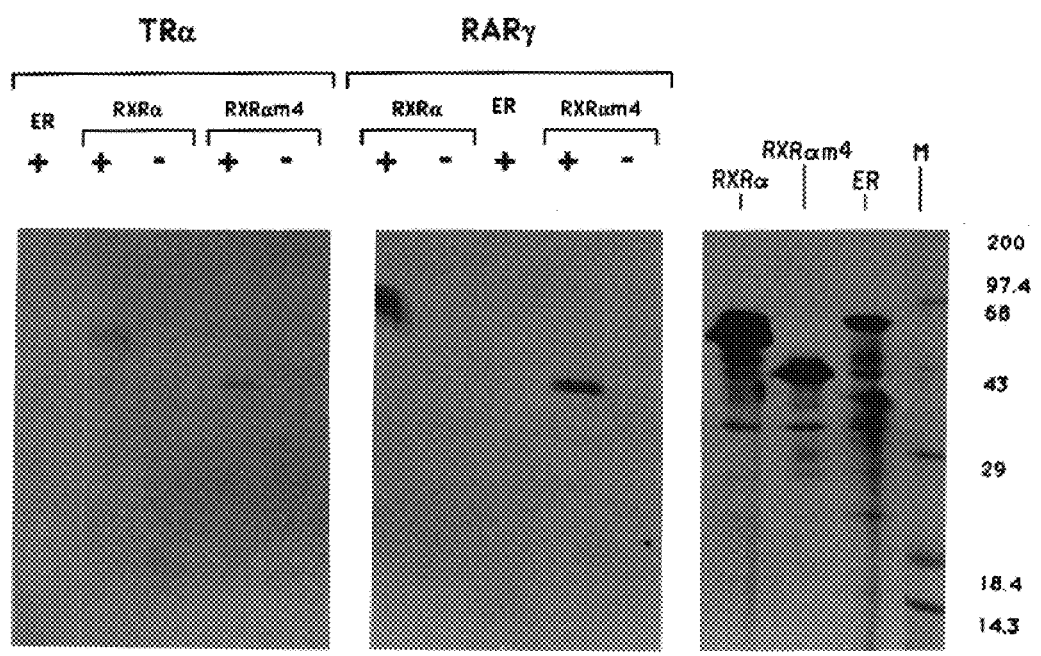

FIG. 8. Direct interaction of RXRα with TR or with RAR.

(a) Affinity column chromatography. To analyze whether RXRα directly interacts with TRs and with RARs in the absence of DNA, TRα and RARγ proteins were synthesized in bacteria using PGEX-2T expression vector (Pharmacia). Purified glutathione S-transferase-TRα or RARγ fusion proteins was also bound to a column (−). $^{35}$S-labelled RXRα and the mutant RXRαm4 synthesized in vitro were then loaded on columns that contained bound glutatione transferase-TRα or -RARγ or glutatione transferase. As a control, in vitro synthesized $^{35}$S-labelled ER was also loaded on a column containing bound glutathione transferase-TRα or -RARγ. After extensive washing with PBS, the bound proteins were eluted with 5 mM reduced glutathione. The eluates were concentrated using centricon 10 and analyzed on a 10% SDS-PAGE. The right panel represents in vitro translation products of RXRα, RXRαm4, and ER. Molecular weight markers (in kd) are also shown.

(b) Immuno-coprecipitation of RXRα by antibody against TR or RAR. $^{35}$S-labelled in vitro synthesized RXRα protein was incubated with partially purified bacterially expressed FLAG-TRα, or FLAG-RARγ (+) or similarly prepared glutathione transferase control protein (−) either in the absence or presence of crosslinker DSP as indicated on the top of the figure. After incubation, either anti-FLAG antibody (F) or preimmune serum (NI) was added. The immune complexes were washed, boiled in SDS sample buffer and separated on a 10% SDS-PAGE. The labelled, in vitro synthesized RXRα protein is shown in the right panel together with the molecular weight marker (in kd).

DETAILED DESCRIPTION OF THE INVENTION

The present invention is based on the core discovery that an RXR can form a heterodimer with other hormone receptors to increase the activity of the receptors. This increase can be in either the hormone receptors' activity or RXR's activity. Since RXRα and β are very closely related, RXRβ has a similar activity to RXRα. Methods employing RXRβ utilize the same methods, conditions etc. as set forth hereinbelow for RXRα.

By "activity" is meant any activity which is affected by the heterodimer formation. Generally, this activity is activation or enhancement of transcription. Generally, the ligand of one or both hormone receptors of the heterodimer enhance the activity.

By "hormone receptor" is meant a receptor of the steroid/thyroid hormone receptor superfamily which forms a heterodimer with an RXR. However, oligodimers are also covered herein. Oligodimers can be tested by the methods set forth hereinbelow. Moreover, any additional receptors not tested can be tested using the methods set forth herein. Proteins having substantially the same sequence and activity of the receptors, such as "RXR", are also included in the definition of hormone receptor. Thus, minor substitutions, deletions and additions can readily be made and tested. Moreover, any receptor consisting essentially of the amino acids of the hormone receptors are included in the definition.

Additionally, since heterodimer formation can be attributed to certain portions of the hormone receptors, molecules containing only those portions are also contemplated. Also, since only certain regions of the receptor may be necessary for activity, i.e., ligand or hormone binding region, heterodimers containing only these portions of the receptors are contemplated.

The activities of the heterodimers can be applied to affect transcription in an in vivo system. Thus, many therapeutic applications, including enhancement or inhibition of transcription, can readily be obtained.

These methods can easily by adapted to use the heterodimers to screen further ligands for their effect on activity. In this way, more effective ligands can be determined. The well known methods used to screen ligands using a single receptor can readily be applied to screen using heterodimers.

A key discovery set forth herein is that different receptors can form heterodimers with selective enhancement or reduction in activity. Thereby specific genes can be regulated using the teachings herein.

The following experimental procedures and results are set forth to exemplify and not limit the invention.

EXPERIMENTAL PROCEDURES

Plasmid Constructions

The constuction of reporter plasmids, TRE-tk-CAT and TRE$_2$-tk-CAT has been described previously (Zhang et al.,1991b). The coding sequences of TRα, TRβ, RARβ, and RARγ were inserted into the multiple cloning sites of the eukaryotic expression vector PECE or pBLUESCRIPT (Stratagene). The construction of these plasmids has been described (Graupner et al., 1989; Zhang et al., 1991b). The TRE-reporter plasmids used, TRE-tk-CAT and TRE$_2$-tk-CAT contain a single or double repeat of the synthetic palindromic sequence TCAGGTCATGACCTGA (SEQ ID NO:14) inserted into the BamHI site at –105 of pBL-CAT2 by using BglII linkers. These constructs have a partially constitutive promoter. Coding sequences of all receptors used in this study were excised from their cloning vectors by appropriate restriction digests and inserted into the multiple cloning sites of the eukaryotic expression vector PECE or pBluescript (Stratagene). The Plasmid constructions were as follows: pECE-RAR-β was obtained by cloning a BamHI-EcoR1 fragment (containing the complete coding region of RAR-β) from clone B1-RAR (B1 designates BlueScript; Stratagene) into the BglII and EcoR1 sites of the pECE expression vector. To obtain pECE-TR-α, a 2-kilobase (kb) EcoR1 fragment of the TR-α clone prbeA12 was cloned into the EcoR1 site of pECE. For construction of PECE-TR-B, a 1.6 kb EcoR1 fragment of the human c-erb-A-B clone was ligated into the EcoRl site of the pECE vector. RARα cDNA was amplified from poly(A) RNA prepared from the squamous cell carcinoma line, SCC-13, by polymerase chain reaction (PCR). The PCR products were cloned into both PECE and pBLUESCRIPT. Two primers (SEQ ID NO: 1 and SEQ ID NO:2) (5'-CGCAGACATGGACACCAAACAT-3'; 5'-CCTCTCCACCGGCATGTCCTCG-3') were used to amplify the N-terminal half of RXRα cDNA from SCC-13 by PCR technique. The SmaI-SalI fragment from PCR product (530 bp) containing the DNA binding domain of the RXRα was used as a probe to isolate RXRα cDNA by screening a λgt11 human placenta cDNA library(obtained from J. Millán; Millán, 1986). Several positive clones were obtained, including full length receptor and the truncated clones, RXRαm3, RXRαm4 and RXRαm5 which were sequenced and show identical sequences as the wild type RXRα. The cDNA clones were subsequently subcloned into the EcoRI site of pBLUESCRIPT and PECE.

To obtain TRα and RARγ deletion mutants, existing restriction enzyme sites on receptors were used to digest receptor cDNAs. The resulting cDNA fragments were purified and cloned into PBLUESCRIPT. TRαm1 and TRαm2 were generated by digesting TRα cDNA with XhoI (1530) and StuI (964), respectively. RARγm1, RARγm2, and RARγm3 were generated by digesting RARγ cDNA with Pst 1 (1469), DraIII (1066), and Sac I (976), respectively (Numbers in brackets indicate the nucleotide position).

RXRα deletion mutants were obtained as following: RXRαm1 and RXRαm2 were generated by digesting RXRα CDNA with StuI (1463) and XmaIII (1231), respectively. RXRαm6 and RXRαm7 were generated by internal deletion using NcoI and BalI, respectively.

The construction of FLAG-containing receptors (FLAG-RXRα, FLAG-TRα, and FLAG-RARγ) was described previously (Hermann et al., 1991; Zhang, et al., 1991a). Briefly, they were constructed by ligating a double-stranded oligonucleotide containing an ATG codon and a DNA sequence encoding FLAG (Arg Tyr Lys Asp Asp Asp Asp Lys) (Hopp et al., 1988) to the N-terminus of receptors. The fusion products were then cloned into PBLUESCRIPT. More specifically, to provide a vector that allows expression of various FLAG-fusion proteins, we cloned into a BglII-SalI-digested PECE the double stranded, synthetic fragment

```
5'-GATCCGCGGCCGCCACCATGGATTACAAGGACGACGACGATAAGATCTG-3'      (SEQ ID NO:15)

3-GCGCCGGCGGTGGTACCTAATGTTCCTGCTGCTGCTATTCTAGACAGCT-5'    (SEQ ID NO:16)
``` encoding the FLAG-sequence under control of the Kozak consensus sequence. The resulting vector (pECE-FLAG) allows fusion of cDNA sequences to FLAG via various sites and the easy transfer of the resulting constructs via the internal NotI and NcoI sites.

Tissue Culture, Transient Transfection, and CAT Assay

CV-1 cells were grown in DME medium supplemented with 10% fetal calf serum (FCS). Cells were plated at $1.0 \times 10^5$ per well in a 24 well plate 16 to 24 hours prior to transfection as described previously (Husmann et al., 1991). A modified calcium phosphate precipitation procedure was used for transient transfection and is described elsewhere (Pfahl et al., 1990). In general, 100 ng of reporter plasmid, 150 ng of β-galactosidase (β-gal) expression vector (pCH 110, Pharmacia), and variable amounts of receptor expression vector were mixed with carrier DNA (BLUESCRIPT) to 1000 ng of total DNA per plate. CAT activity was normalized for transfection efficiency by the corresponding β-galactosidase activity (Pfahl et al., 1990). According to this method, one milliter precipitate was prepared in the following way: 2 μg reporter plasmid, 0.1 to 1 μg receptor expression vector, 3 gg β-galactosidase control plasmid (pCH110, Pharmacia, Piscataway, N.J.), and Bluescript plasmid to obtain a total amount of 20 μg DNA were dissolved in a total volume of 450 μl water. To this mixture 50 μl of 2.5 M $CaCl_2$ was added and mixed carefully. Five hundred microliters of BBS buffer, pH 6.95 [50 mM N,N-bis(2-hydroxyethyl)-2-aminoethanesulfonic acid, 250 mM NaCl, 1.5 mM $Na_2HPO_4$], was added and mixed by inverting the tube repeatedly. The reaction mixtures were then incubated at room temperature for 10–15 min. During this time a very fine precipitate forms. One milliliter of this precipitate suspension was added per plate followed by incubation at 37° and 4% $CO_2$ for 14–18 hr. The medium was then exchanged with DMEM containing 10% charcoal-treated FCS with or without ligand. Incubation was continued for 24 hr at 37° and 6% $CO_2$. After that time, cells were harvested in HBS buffer, pH 7.1 (25 mM HEPES, 140 mM NaCl, 0.75 mM $Na_2HPO_4$), pelleted by centrifugation, and resuspended in 130 μl of 250 mM Tris-HCl (pH 7.8). The cells were lysed by 3 freeze/thaw cycles. Cellular debris was removed by centrifugation. The cell extract obtained can be used either directly for enzyme assays or may be stored at −20°.

The β-galactosidase assay was carried out in principle as described but was modified to be run in microtiter plates. A reagent mix was freshly prepared by combining the following stock solutions (calculated per assay): 100 μl of 0.1 M sodium phosphate buffer, pH 7.3; 1.5 μl of 100× magnesium solution (0.1 M $MgCl_2$, 5 M 2-mercaptoethanol); and 33 μl ONPG solution (4 mg o-nitrophenyl-β-D-galactopyranoside per 1 ml sodium phosphate buffer). Fifteen microliters of extract was pipetted into each microtiter well (using 15 μl of 250 mM Tris-HCl, pH 7.8, for background correction). After addition of 135 μl of the reagent mix to each well, the plate was incubated at 37° until a yellow color was visible (30–60 min). The reaction was stopped by adding 150 μl of 1 M $Na_2CO_3$. Absorbance was measured in a microtiter plate reader at 405 nm.

Chloramphenicol acetyltransferase (CAT) activity was determined by either the classic assay or a modified assay using [$^3$H]acetyl-coenzyme A as substrate. The modified assay was more sensitive and less time-consuming. The assay was based on mixed-phase scintillation measurement where only the product, $^3$H-acetylated chloramphenicol, partitions out of the urea-containing aqueous phase into the nonpolar scintillation liquid. The substrate [$^3$H]acetyl-CoA remained in the aqueous phase and was therefore not measured. For the reaction, 30 μl of the cell extract was combined with 20 μl of 250 mM Tris-HCl, pH 7.8 20 μl chloramphenicol solution (5 mM chloramphenicol in 250 mM Tris-HCl, pH 7.8), and 20 μl [$^3$H]acetyl-CoA solution (150 uM [$^3$H]acetyl-CoA, 20 uCi/ml, in 75 uM HCl). For background activity determinations, the chloramphenicol solution was substituted by the Trig buffer. The reaction mixtures were incubated at 37° for 1 to 2 hr. The reaction was stopped by addition of 1 ml of 7 M urea. The mixture was transferred to a scintillation vial containing 4.5 ml scintillation cocktail (0.8% 2,5-diphenyloxazole in toluene). After shaking and phase separation, counts per minute (cpm) were determined. Counts per minute corrected for background and β-galactosidase activity represent the specific CAT activity.

Preparation of Receptor Proteins cDNAs for RXRα, RARα, RARα, RARγ,TRα, TRβ, FLAG-RXRα, FLAG-TRα, FLAG-RARγ and the deletion mutants cloned into pBluescript were transcribed by using T7 and T3 RNA polymerases, and the transcripts were translated in the rabbit reticulocyte lysate system (Promega) as described (Pfahl et al., 1990: Zhang et al., 1991b). To synthesize RAR protein in vitro, we take advantage of the presence of T7 or T3 RNA polymerase promoter sites in the Bluescript vector. The RAR construct was linearized with an appropriate restriction enzyme that cleaves "downstream" of the RAR insert. The linearized plasmid DNA was then treated with 200 Mg/ml proteinase K at 37° for 30 min, followed by phenol/chloroform (1:1) extraction and ethanol precipitation. One microgram of template DNA was used for in vitro transcription in a 50-μl reaction mixture containing 40 mM Tris-HCl, pH 8.0, 8 mm $NgCl_2$, 2 mM spermidine, 30 mM dithiothreitol (DDT), 50 mM NaCl, 0.4 mM of each ribonucleotide, 1 unit RNase inhibitor (Stratagene), and 10 units of either T7 or T3 RNA polymerase. The transcription reaction was incubated at 37° for 30 min. To remove the DNA template, the reaction was diluted 10-fold with 40 mM Tris, pH 7.5, 6 mM $MgCl_2$, 10 mM NaCl, and incubated with 1 unit of RNase-free DNase I (BRL) at 37° for 15 min. The efficiency of transcription can be monitored by agarose gel electrophoresis.

RAR protein can be easily synthesized in vitro utilizing the rabbit reticulocyte translation system (Promega, Madison, Wis.), RNA template was incubated at 67° for 10 min and immediately cooled on ice to eliminate any secondary structure. Approximately 1 µg RNA was then mixed with 35 µl nuclease-treated reticulocyte lysate, amino acid mix (20 uM of each), and 1 unit of RNase inhibitor in a total volume of 50 µl. The translation reaction was carried out at 30° for 60 to 90 min. The synthesized receptor protein was then aliquoted and can be stored at −70°. Alternatively, 2.5 µl [$^{35}$S]methionine (>1200 Ci/mol, New England Nuclear, Boston, Mass.) was included in the translation reaction. The labeled receptor protein can then be analyzed by sodium dodecyl sulfate-polyacrylamide gel electrophoresis (SDS-PAGE) to determine the translation efficiency. The relative amounts of the translated proteins was determined by separating the $^{35}$S-methionine labelled proteins on SDS-polyacrylamide gels, quantitating the amount of incorporated radioactivity and normalizing it relative to the content of methionine residues in each protein. In vitro synthesized FLAG-containing receptor proteins were checked for corrected sizes and antigenic specificity by immunoprecipitation with anti-FLAG antibody (obtained from M. Leahy, Immunex, Seattle, Wash.) followed by SDS-polyacrylamide gel electrophoresis.

cDNAs for RXRαm3, RXRαm4 and RXRαm5 cloned into PBluescript were also translated in vitro. The translation start sites of these clones used the internal ATG sequences at 28, 61 and 198 amino acid position, respectively, as determined by the SDS-PAGE analysis of the $^{35}$S-labelled translation products.

To prepare TRα and RARγ fusion proteins, FLAG-TRα and FLAG-RARγ cDNAs were cloned in frame into the expression vector pGex-2T (Pharmacia). The proteins were expressed in bacteria using the procedure provided by the manufacturer. Proteins were purified on a prepacked glutathione sepharose 4B column (Pharmacia), and checked by gel retardation assays and western blot with anti-FLAG antibody.

Preparation of Specific DNA Fragments

The TRE used in the experiments was a 16-bp perfect palindromic TRE (SEQ ID NO:4) (TCAGGTCATGACCTGA) (Glass et al., 1988). An oligonucleotide flanked by a BglII adaptor sequence was synthesized (Applied Biosystems DNA Synthesizer) and purified by polyacrylamide gel electrophoresis. Oligonucleotides were annealed and were radioactively labeled using the Klenow fragment of DNA polymerase. TRE/OP is an oligonucleotide consisting of two TRE half-sites with a 4 bp spacer (SEQ ID NO:5) (GATCCTGACCTGAGATCTCAGGTCAG). TRE/half is an oligonucleotide consisting of one TRE half-site (SEQ ID NO:6) (GATCTCAGGTCA). βRARE is the direct repeat of RA response element present in RARβ promoter (SEQ ID NO:7) (AGGGTTCAGGCAAAGTTCAC). ERE is the perfect palindromic ER response element (SEQ ID NO:8) (TCAGGTCACTGTGACCTGA). These oligonucleotides are all synthesized with a BglII adaptor sequence. Labeled DNA probes were purified by gel electrophoresis and used for the gel retardation assay.

Preparation of Cell Extracts

Cell extracts were prepared from CV-1 cells in a buffer containing 20 mM Hepes, pH 7.9, 0.4 M KCl, 2 mM DTT and 20% glycerol as described (Zhang et al., 1991a).

Gel Retardation Assays

In vitro translated receptor protein (1 to 5 µl depending on the translation efficiency) was incubated with the $^{32}$P-labeled oligonucleotides in a 20-µl reaction mixture containing 10 mM hepes buffer, pH 7.9, 50 mM KCl, 1 mM DTT, 2.5 mM MgCl, 10% glycerol, and 1 µg of poly(dI-dC) at 25° C. for 20 minutes. In general, relative low receptor concentration was used to obtain the clear effect of heterodimer formation. The reaction mixture was then loaded on a 5% nondenaturing polyacrylamide gel containing 0.5× TBE (1×TBE=0.089 M TRIS-borate, 0.089 M boric acid, and 0.002 M EDTA). To analyze the effect of RXRα or the nuclear proteins on receptor DNA binding activity, RXRα or the cell extracts were preincubated with receptor protein at room temperature for 10 minutes before performing the DNA binding assay. When antibody was used, 1 µl of the antiserum was incubated with the specific translation products at room temperature for 45 minutes before performing the experiments described above.

Affinity column chromatography

To analyze the interaction between RXRα and TRα or and RARγ, purified FLAG-TRα or FLAG-RARγ fusion proteins were loaded on the prepacked glutathione sepharose 4B columns. For control, the vector protein (glutathione S-transferase) prepared under the same conditions was also loaded on the separate columns. The columns were washed extensively with PBS with 1% TRITONX-100. $^{35}$S-labelled in vitro synthesized RXRα, RXRαm4 and ER proteins were applied to the columns. Columns were then washed extensively 3 times with 10 ml PBS. The bound protein was eluted with 50 µM Tris pH 8 containing 50 µM TRIS pH 8 containing 5 µM glutathione. Eluates were then concentrated by using a Centricon 10 microconcentrator, and analyzed by denaturing polyacrylamide gels.

Immunoprecipitation

Twenty microliters of reticulocyte lysate containing in vitro translated $^{35}$S-labelled RXRα were incubated with 5 µl (approximately 0.2 µg) of partially purified bacterially expressed FLAG-TRα or FLAG-RARγ fusion proteins or similarly prepared glutathione transferase control protein in 100 µl buffer (containing 50 mM KCl and 10% glycerol) for 15 min. at room temperature. When cross-linker was used, we added 2 µl of 100 mM DSP and continued the incubation at room temperature for 10 min. The reactions were then incubated with 1 µl of anti-FLAG antibody or preimmune serum for 2 hrs. on ice. Immunocomplexes were precipitated by adding 60 µl of protein-A-sepharose slurry and mixing continuously in the cold room for 1 hr. Protein-A-sepharose was saturated in TBS buffer (TRIS-buffered saline) or in RIPA buffer when cross-linker was used. The immunocomplexes were washed four times with NET-N buffer (20 mM TRIS, pH 8.0,100 mM NaCl, 1 mM DTT, 0.5% NP-40) or five times with RIPA buffer when DSP was used, and resuspended in SDS sample buffer containing 15% β-mercaptoethanol, boiled and resolved by SDS-polyacrylamide gel electrophoresis. The gels were fixed, dried and visualized by autoradiography.

Results

RXRα enhances DNA binding of TRs and RARs

Figure 1B:
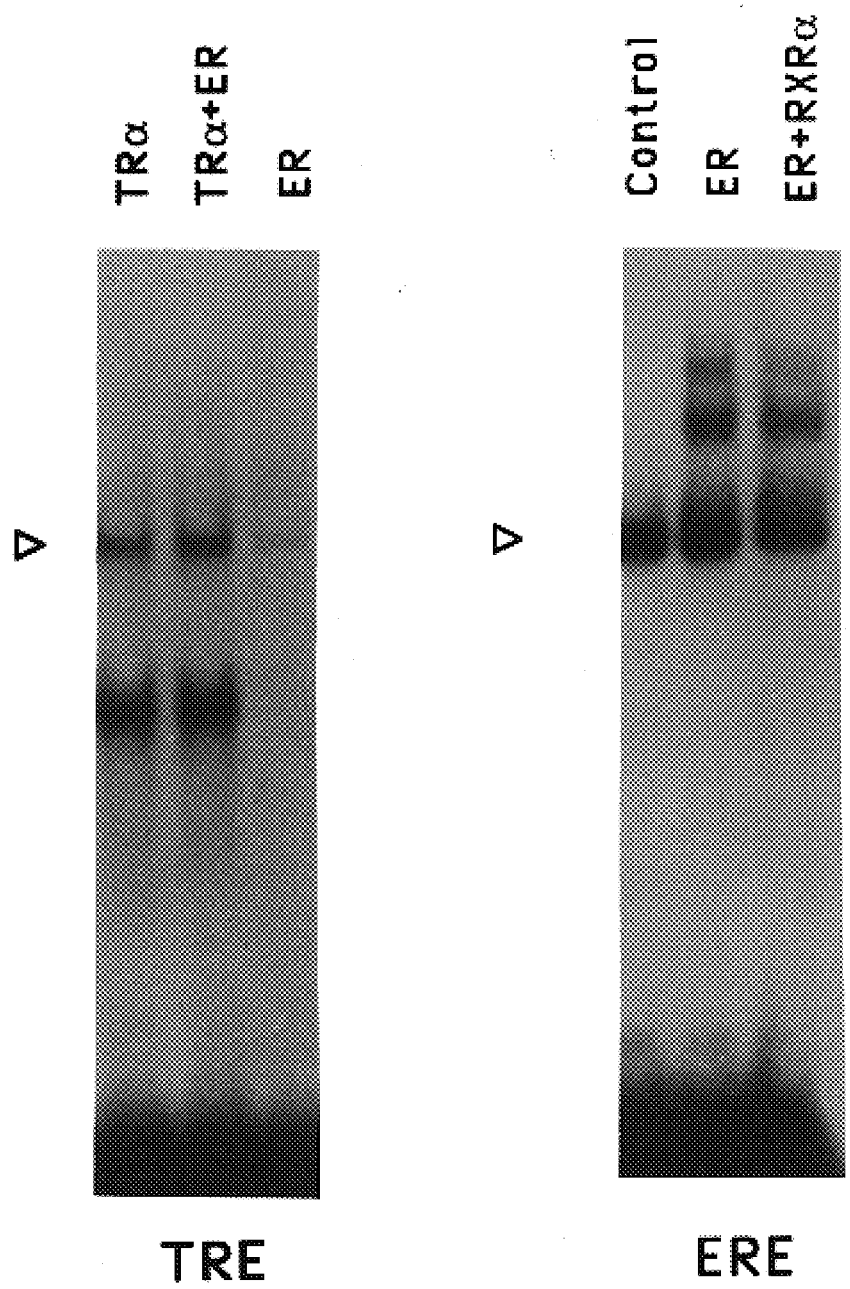

Previous data from us (Zhang et al., 1991a) and others (Lazar and Berrodin, 1990; Glass et al., 1990; Murray and Towle, 1989; Burnside et al., 1990; Rosen et al., 1991) suggested that TRs and RARs bind more efficiently to their response elements by binding as heterodimers or heterooligomers. Since proteins from nuclear extracts that enhance TR and/or RAR DNA binding have not been defined, we investigated the possibility that TRs can bind with increased efficiency to the palindromic TRE when complexed with other nuclear receptor proteins, in particular those that bind and activate the same or related response elements. Using the gel retardation assay, we observed that TRα bound to the TRE as one major complex which migrates faster than the nonspecific band seen with unprogrammed reticulocyte lysate (FIG. 1a). This specific complex has been previously demonstrated to represent the binding of a TRα monomer (Zhang et al., 1991a; Forman and Samuels, 1991). When TRα was mixed with RXRα, a dramatic increase in DNA binding was seen. A prominent complex which migrated slower than the nonspecific complex was observed while the faster migrating TRα complex disappeared (FIG. 1a). The strong binding complex was observed at concentrations at which RXRα by itself did not form visible complexes with the TRE (FIG. 1d). The effect of RXRα was specific since no significant increase in TRα binding to the TRE or change of TRα binding pattern could be observed when it was mixed with RARα (FIG. 1a) or estrogen receptor (ER) (FIG. 1b). In addition, when RXRα was mixed with ER and labelled ERE (FIG. 1b), no increased binding or slow electrophoretic mobility complex was seen. Interestingly, when TRα isoform TRα-2 was used, the formation of a low electrophoretic mobility complex was not observed either (FIG. 1a). These data suggest that TRα and RXRα bind as heterodimers at least by an order of magnitude more effectively to the palindromic TRE than by themselves. To investigate whether RXRα can also affect the binding of other nuclear receptors, RXRα was mixed with in vitro synthesized TRβ, RARα, RARβ and RARγ receptor proteins (FIG. 1a). Similar to TRα, the complex formed between TRβ and TRE was upshifted by RXRα. In the case of RARα, RARβ and RARγ, specific protein-DNA complexes which migrated slower than the nonspecific complex were observed only in the presence of RXRα, while by themselves RARs did not form detectable complexes with the TRE under the conditions used. Very similar results were also obtained with bacterially produced TRα and RARγ (data not shown). The mobility of the slow migrating complexes formed between RXRα and TRα was very similar to that formed between TRα and nuclear protein(s) (FIG. 1c) from CV-1 cells previously reported by us (Zhang et al., 1991a). This suggests that the protein(s) found in CV-1 cells might be RXRα or related protein(s). Next, we investigated the effect of T3 or RA on the interaction between RXRα and TRs or RARs (FIG. 1d). We observed no clear influence of these hormones on the formation of the slow migrating complexes when TRα and RARα were studied although $T_3$ slightly increases the migration rate of the TRα complex. Similar results were also obtained when TRβ, RARβ and RARγ were analyzed (data not shown).

RXRα forms a complex with TRs and RARs

The observation that TR is upshifted by RXRα but not by RAR and ER and the fact that RAR binds to the TRE strongly only in the presence of RXRα but not of TR, strongly suggested that RXRα interacts with TRs and RARs to form heterodimers or larger complexes which interact very effectively with the palindromic TRE. It is unlikely that RXRα catalyzed formation of TR and RAR homodimers since at high TRα concentrations, we have observed a TRα dimer complex (Zhang et al., 1991a) which comigrates with the nonspecific band of the reticulocyte lysate, and which is at a different position from the complex we observed here in the presence of RXRα. The slow migrating complex observed here cannot represent the binding of RXRα homodimers either, since the migration of the complex is different depending on which receptor is mixed with RXRα (FIG. 1a).

Figure 2A:
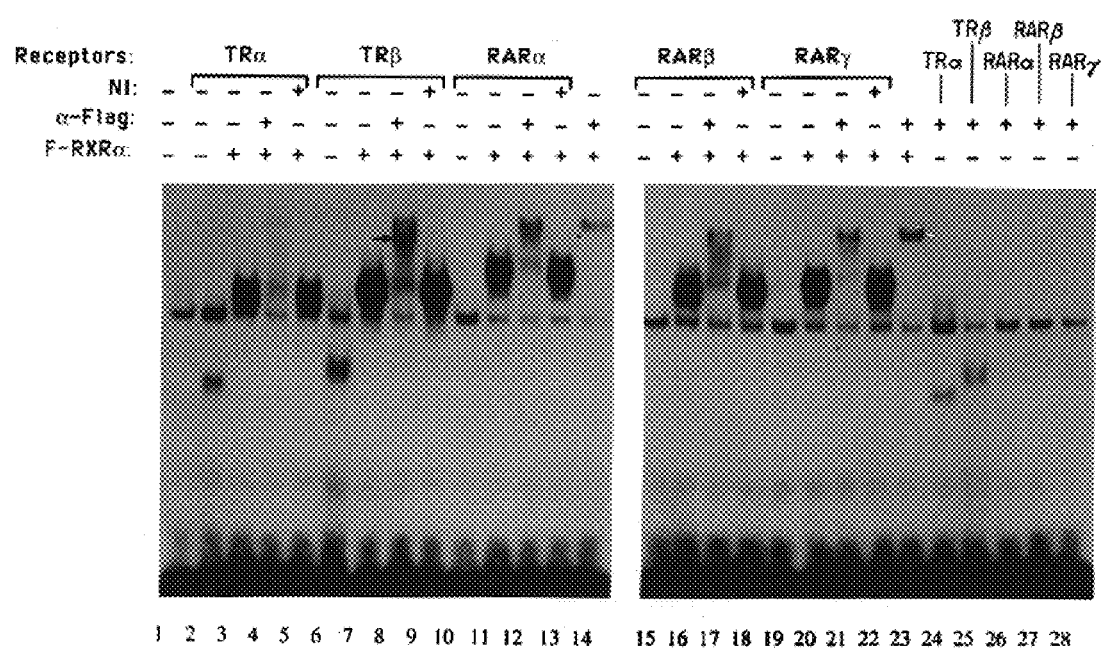
Figure 2B:
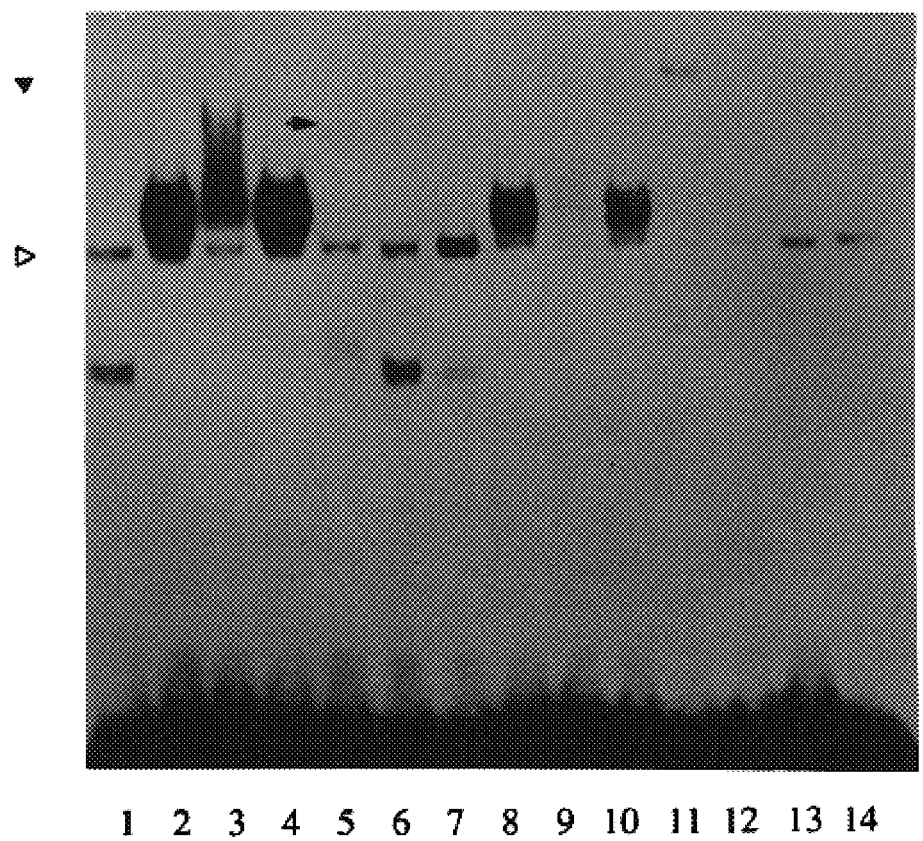
Figure 2C:
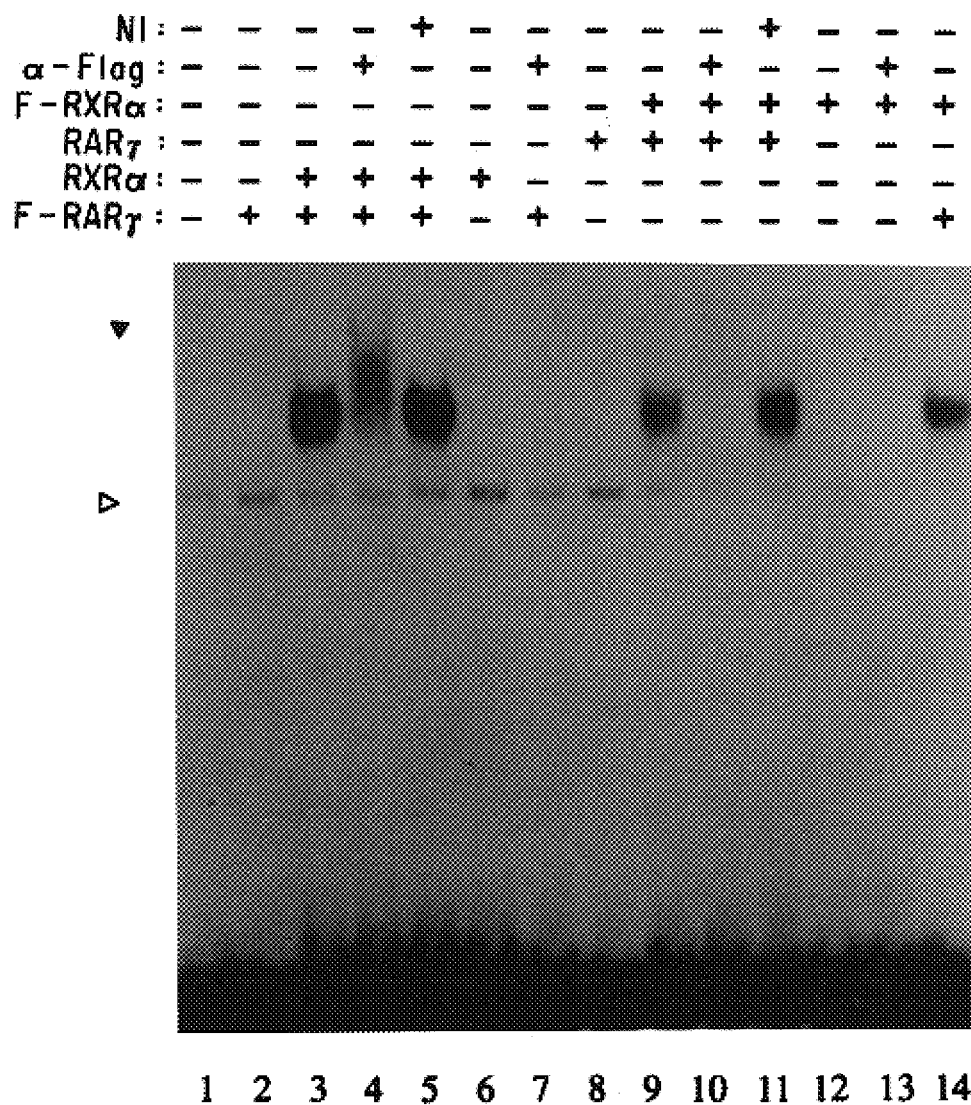

To examine more directly the components of the prominent upshifted complexes, we used RXRα, TRα and RARγ derivatives that contained an eight-amino-acid epitope (FLAG) at the amino-terminal end of these receptors (FLAG-RXRα, FLAG-TRα and FLAG-RARγ, respectively) which can be recognized by a specific monoclonal antibody (Hermann et al., 1991; Zhang et al., 1991a). The behavior of these receptor derivatives was indistinguishable from that of the wild-type receptor in both transcriptional activation (Zhang et al., 1991c; data not shown) and DNA binding activity (FIG. 2). When FLAG-RXRα was incubated with anti-FLAG antibody, we observed a specific complex (FIG. 2a, lanes 14 and 23; FIG. 2b, lane 11; FIG. 2c, lane 13) which was not observed when preimmune serum was used (FIG. 2b, lane 12). The complex may represent the binding of the antibody-catalyzed FLAG-RXRα homodimer or homooligomers. These data therefore suggest that RXRα by itself can not efficiently dimerize and bind to DNA. Similar antibody-induced dimerization has been observed for other receptors (Hermann et al., 1991; Zhang et al., 1991a). When FLAG-RXRα was incubated with TRs and RARs, it behaved essentially like RXRα, forming prominent slow migrating complexes (FIG. 2a, lanes 3, 7, 11, 16 and 20). These complexes were strongly reduced when anti-FLAG antibody was added (FIG. 2a, lanes 4, 8, 12, 17 and 21). At the same time a higher molecular weight complex (indicated by the solid triangle) appeared. The reduction of the slow migrating complexes was observed when antibody was added either before or after both receptors were mixed (data not shown). The effect of antibody was specific in that the binding of these complexes was not changed when preimmune serum was used (FIG. 2a, lanes 5, 9, 13, 18 and 22), and the nonspecific binding of unprogrammed reticulocyte lysate (indicated by open triangle) was not affected by the antibody. In addition, the effect of anti-FLAG antibody was specific towards FLAG-RXRα since it did not influence the binding of TRs and RARs (FIG. 2a, lanes 24–28) and RXRα (FIG. 2b, lane 13). The migration of the faint higher molecular weight complex that appeared in the presence of antibody was dependent on the TR or RAR isoform used. This complex migrated at the same position as the antibody-catalyzed RXRα homodimer (FIG. 2a, lanes 14 and 23), suggesting that it may represent the binding of antibody-catalyzed FLAG-RXRα homooligomer. However, the intensity of this band was much weaker than the band observed in the absence of antibody. The inhibition of the slow migrating complexes in the presence of anti-FLAG antibody suggests that the antibody interacted with RXRα-TRs or RXRα-RARs complexes, resulting in the formation of larger complexes which have strongly reduced or altered affinity to DNA. When TRβ was assayed in the presence of FLAG-RXRα and anti-FLAG antibody (FIG. 2a, lane 8), we clearly observed an additional complex (indicated by arrow). This complex migrated differently from the antibody-catalyzed FLAG-RXRα homodimer complex, and therefore may represent the binding of the antibody-upshifted FLAG-RXRα/TRβ heterodimer. Together, these data provide strong support for the assumption that the slow migrating complexes contain RXRα. More direct evidence comes from RXRα deletion mutant studies in which we show that the migration rate of the complexes depends on the size of the RXRα protein (FIG. 5).

We show in FIG. 1 that the slow migrating complexes migrate differently depending on which TR or RAR isoform is mixed with RXRα, suggesting that the slow migrating complexes contain TR or RAR. To directly test this, we used FLAG-TRα and FLAG-RARγ (FIGS. 2b and 2c). For comparison, the effect of anti-FLAG antibody on FLAG-RXRα/TRαand FLAG-RXRα/RARγ binding is shown on the same gel (FIG. 2b, lanes 7–12; FIG. 2c, lane 8–13). The FLAG-TRα behaved essentially as TRα, forming one specific complex (FIG. 2b, compare lane 1 and lane 7), which now can be upshifted by anti-FLAG antibody (FIG. 2b, lane 5; indicated by arrow) but not by preimmune serum (lane 6). When FLAG-TRα mixed with RXRα a slow migrating complex appeared (lane 2) which is similar to the complex formed by TRα and FLAG-RXRα (lane 8). The appearance of this slow migrating complex was inhibited when anti-FLAG was added (lane 3). The inhibition was specific since the binding was not affected when preimmune serum was used (lane 4) and the nonspecific binding of unprogrammed reticulocyte lysate (indicated by open triangle) was not changed by the antibody. In addition, the antibody did not influence the binding of wild type RXRα or TRα (lanes 13 and 14). Similar to the effect of the antibody with FLAG-RXRα and TRs or RARs (FIG. 2a), we also observed the appearance of weak slow mobility complexes when incubating antibody together with FLAG-TRα and RXRα. When FLAG-TRα was replaced with FLAG-RARγ, similar inhibition effect of anti-FLAG antibody on FLAG-RARγ/RXRα binding was also seen (FIG. 2c). Thus, taken together, these data strongly suggest that slow migrating prominent band observed in the presence of RXRα contain both RXRα and TR or RAR.

A specific dimeric response element is required for heterodimer interaction

Figure 3A:
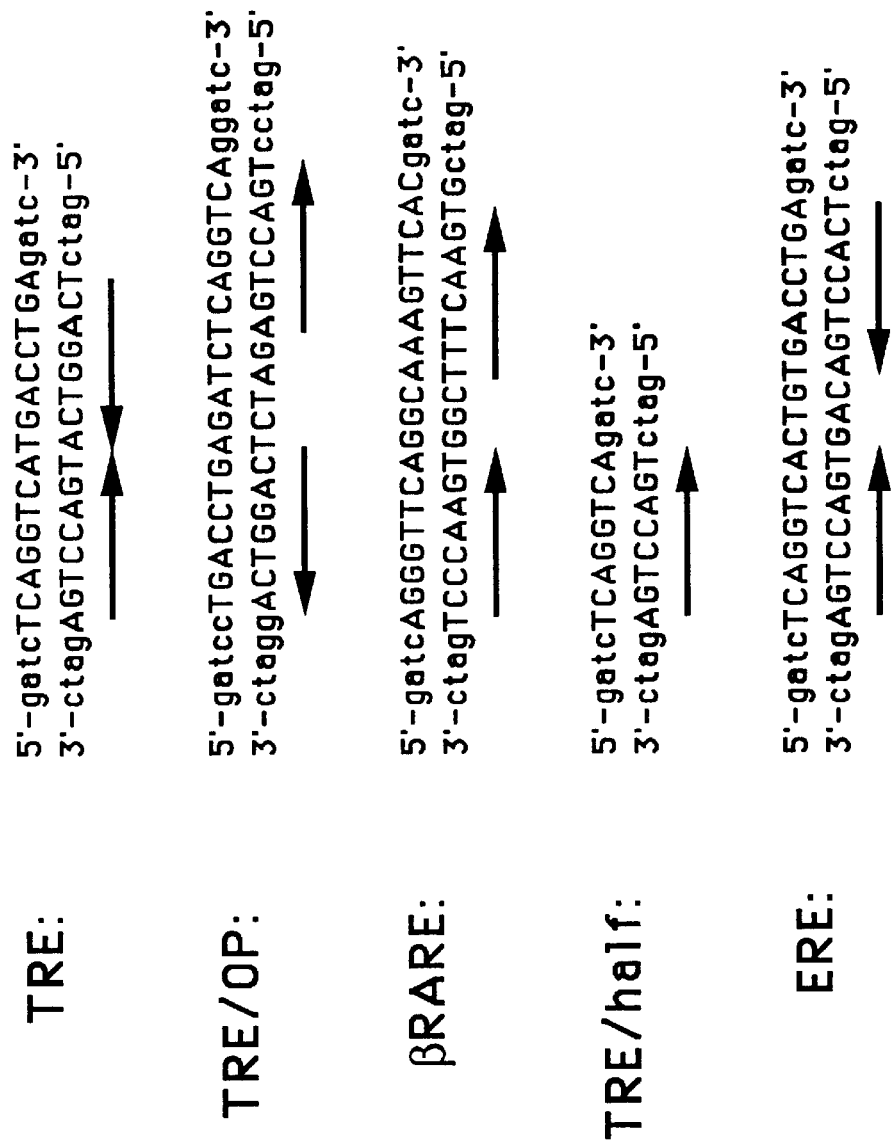
Figure 3B:
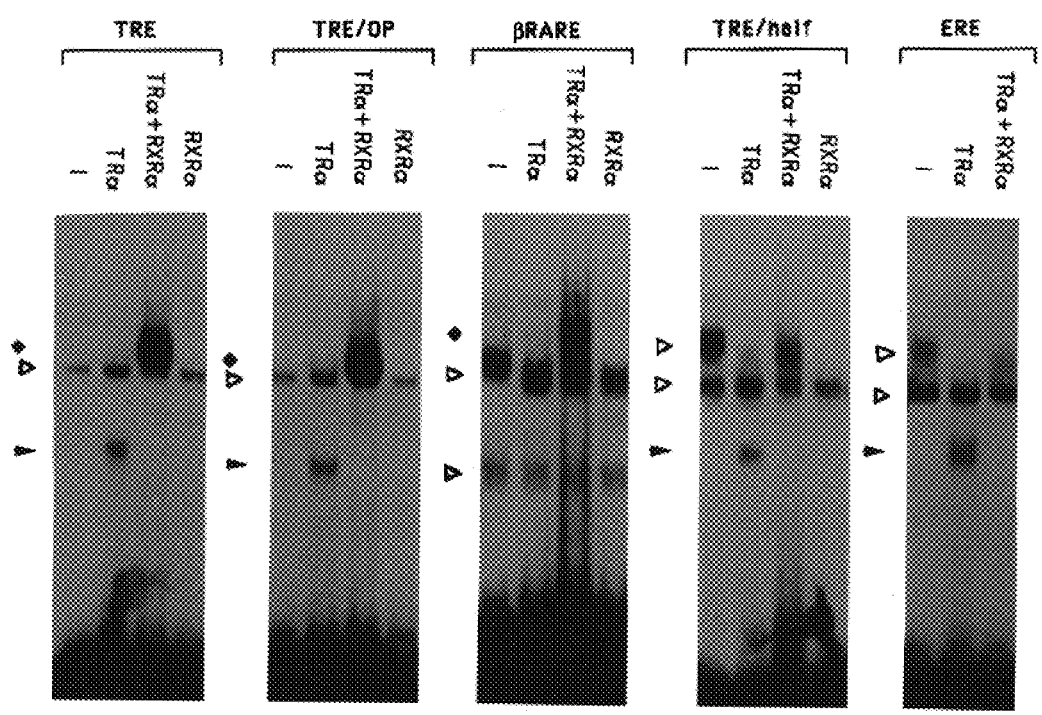

To investigate the DNA sequence requirements for effective heterodimer binding, gel retardation assays were carried out using several TRE related sequences: an inverted repeat of the TRE (TRE/OP); a TRE half-site; the βRARE, a retinoic acid response element (Hoffmann et al., 1990; de Thé et al., 1990); and the estrogen response element (ERE, KLEIN-HITPASS et al, 1986) (FIG. 3a). RXRα alone did not bind to these DNA sequences at the concentration we used. However, when it was mixed with TRα, a specific slow migrating complex was observed on the TRE, TRE/OP, and the βRARE (FIG. 3b). Similar to the palindromic TRE, TRα binds to the inverted repeat of the TRE as one complex which was strongly enhanced and upshifted in the presence of RXRα. In case of the βRARE, TRα alone shows no visible binding but binds strongly when RXRα is present. Binding of TRα to the half-site is approximately as efficient as to the palindromic TRE in the absence of RXRα. However, this binding was abolished in the presence of RXRα, suggesting that a TRα/RXRα complex is formed but that a dimeric response element is required for heterodimer interaction. Interestingly, TRα also binds to the ERE, a response element identical to the palindromic TRE except for the 3 bp spacing in the center (FIG. 3a). However, when RXRα was added, the binding of TRα to ERE was abolished. The inhibition of TRα binding to the ERE by RXRα could also be due to the interaction between TRα and RXRα in solution and formation of a heterodimer which has reduced affinity or does not bind to the ERE. Together these data demonstrate that a dimeric recognition sequence must be present for effective heterodimer binding and that heterodimer binding appears to be restricted to $T_3$/RA responsive elements. Our data suggest in addition, that RXRα can enhance receptor binding to quite different dimeric response elements, indicating a broad functional role for RXRα.

The carboxyterminal end of TR and RAR is necessary for interaction with RXRα

Figure 4A:
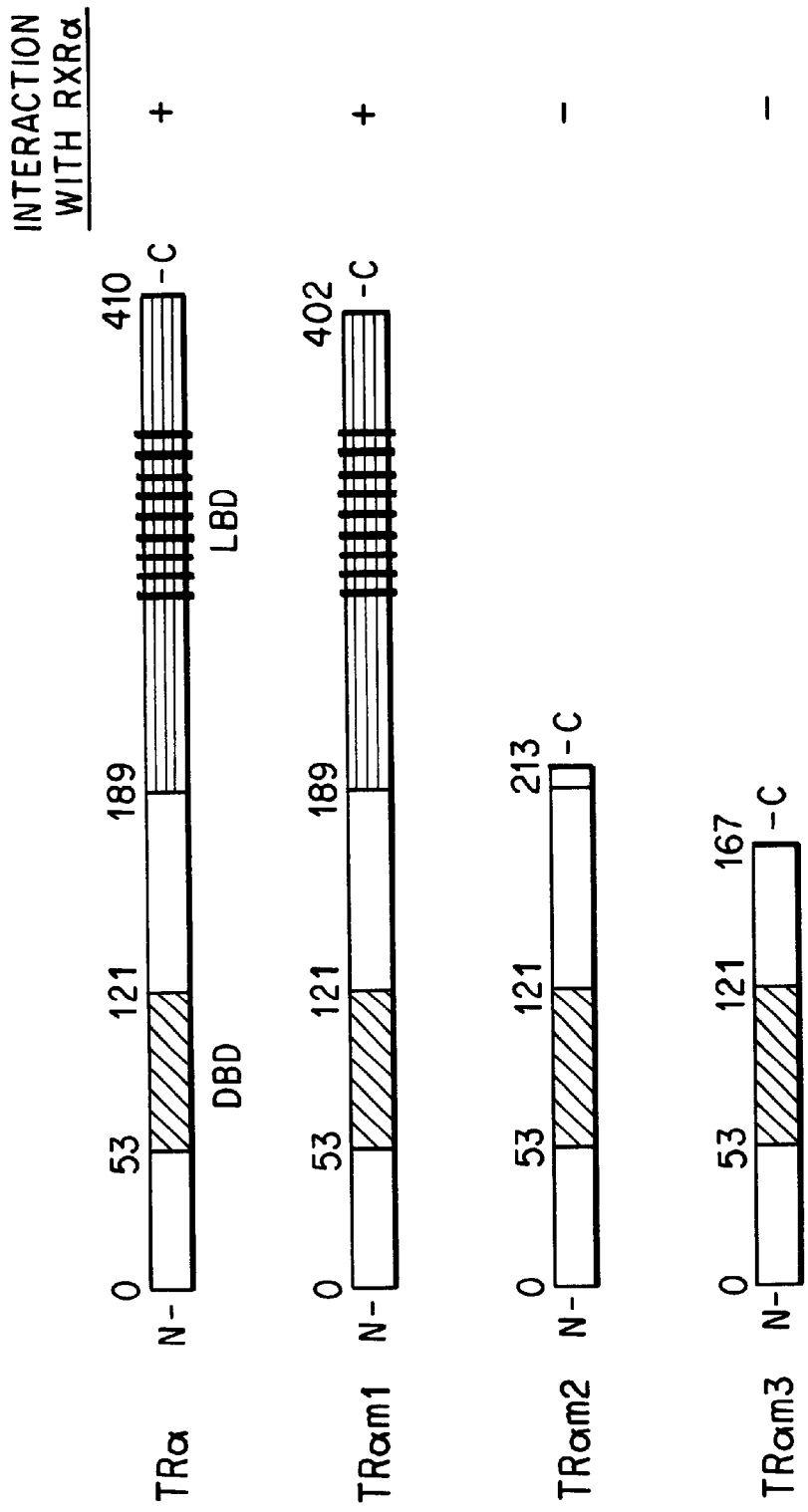
Figure 4B:
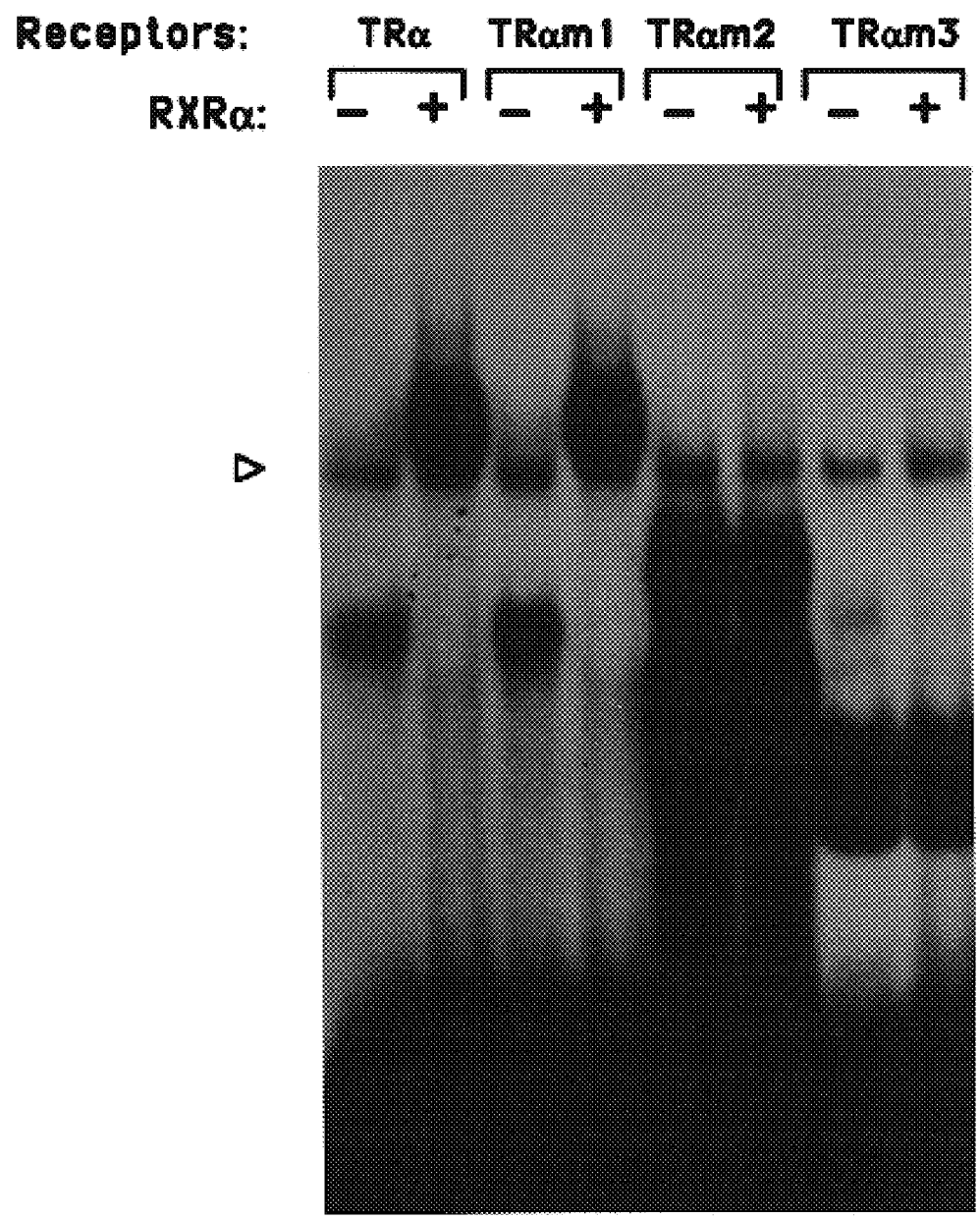
Figure 4C:
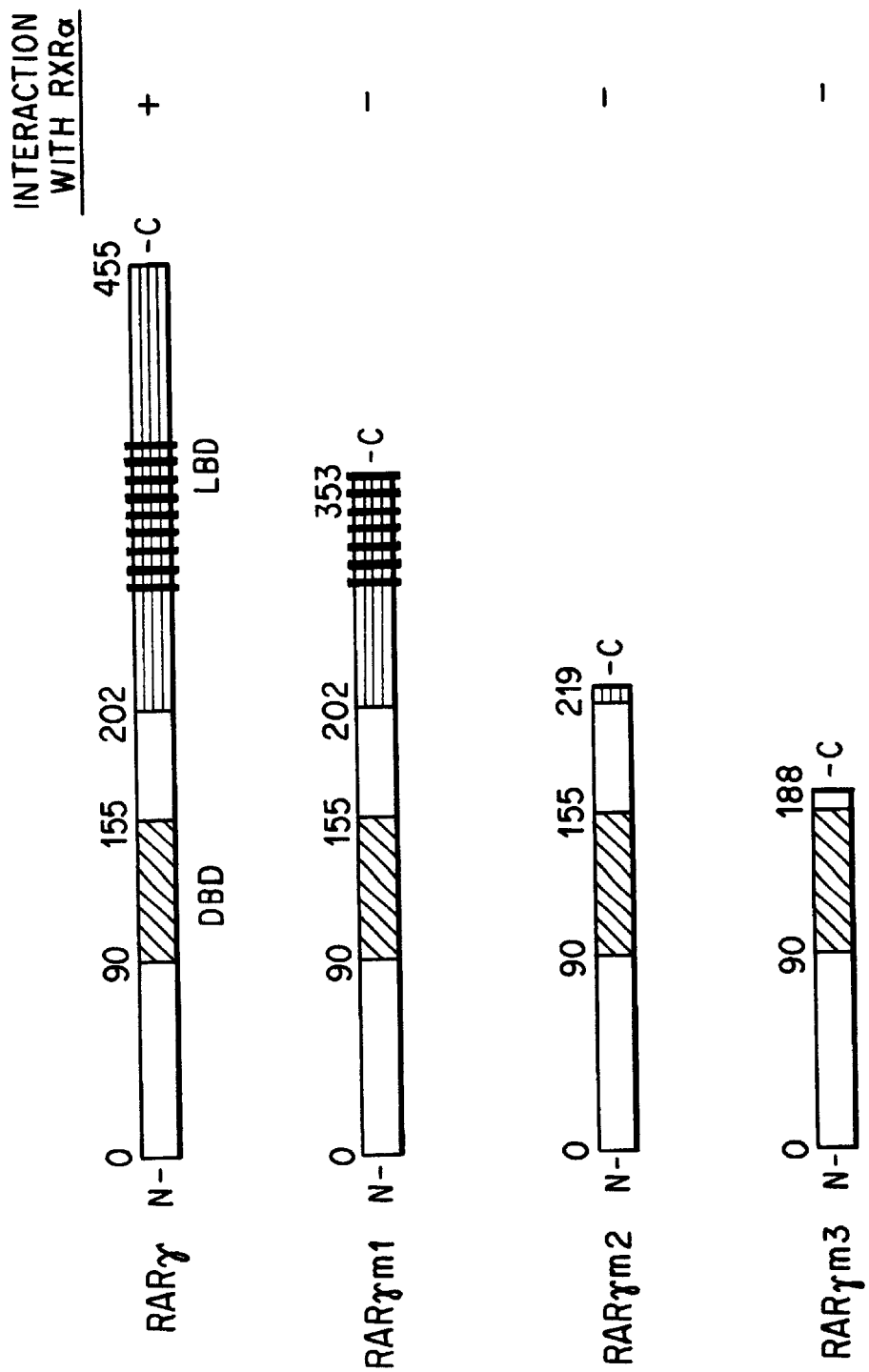
Figure 4D:
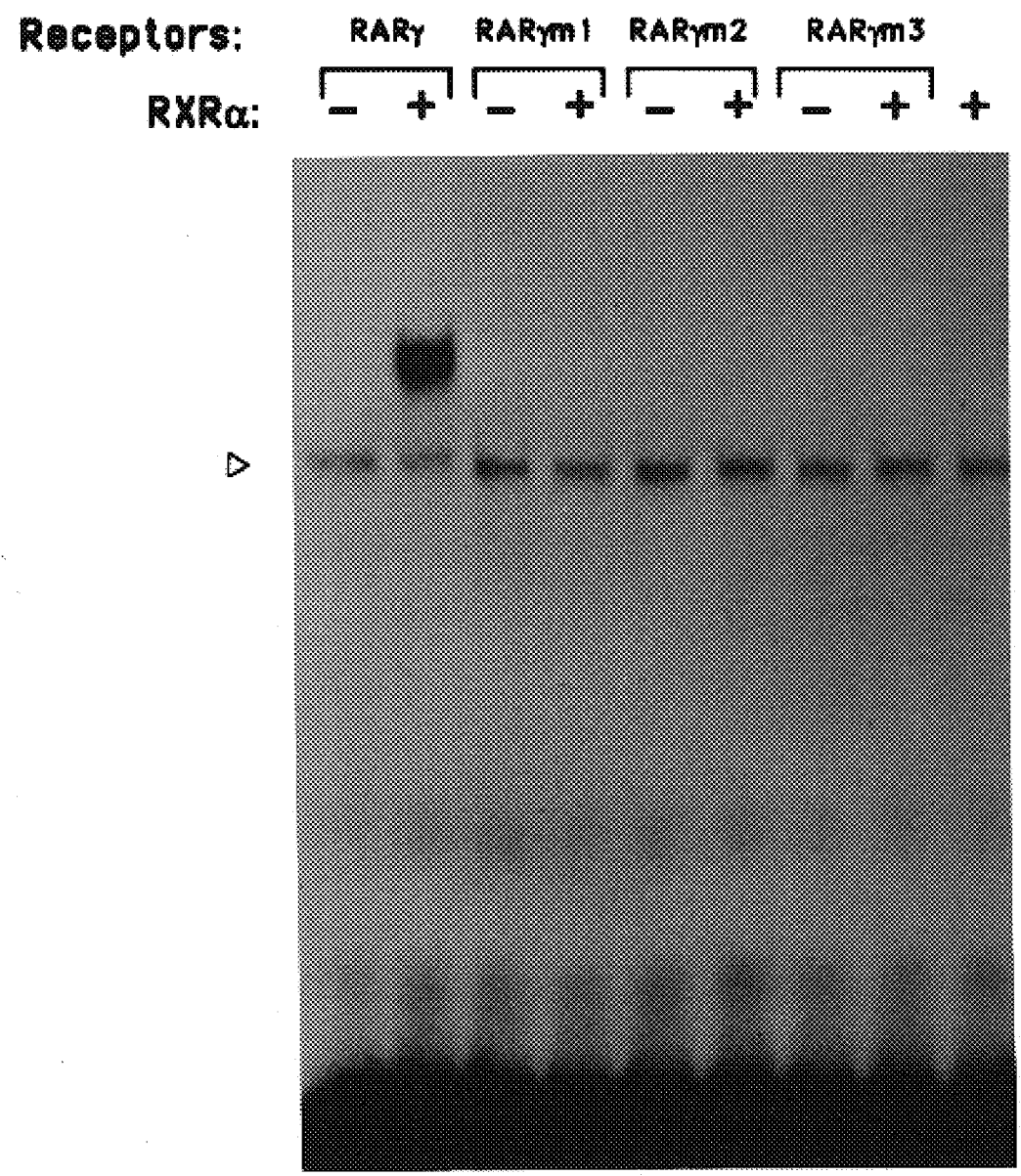

To delineate regions of the TRs and RARs required for RXRα interaction, a number of TRα and RARγ deletion mutants were investigated (FIGS. 4a, 4c). The deletion of 8 amino acids from the TRα carboxyterminus did not affect TRα-RXRα interaction, however, deletion of 197 amino acids (TRαm2) or 243 amino acids (Trαm3) abolished TRα-RXRα complex formation. The TRαm2 and m3 mutants bound effectively to the TRE (FIG. 4b) as reported previously and are able to dimerize or oligomerize since several complexes can be observed (Zhang et al., 1991a). Similar results were also observed with RARγ deletion mutants (FIGS. 4c, 4d). Wild type RARγ and the mutants do not exhibit visible binding under the conditions used. As shown before, a strong DNA binding complex was observed when RXRα protein was mixed with RARγ (FIG. 4d). However, deletion of 102 amino acid from the carboxyterminus (RARγml) completely abolished the binding of this complex. Other carboxyterminal deletion mutants behaved similarly to the RARγml (FIGS. 4c,4d). Our results on the TR mutants are consistent with our observation that TRα-2 which has an altered carboxyterminal region (Benbrook and Pfahl, 1987) also does not form a low electrophoretic mobility complex with the TRE in the presence of RXRα (FIG. 1a). Mutational analysis of other receptors, including TRβ, RARα and RARβ, revealed that the carboxyterminal region of these receptors is also important for their interaction with RXRα (data not shown). These results therefore indicate that the carboxyterminal region TRα and RARγ is critical for interaction with RXRα.

RXRα regions required for nuclear receptor interaction

To delineate regions of RXRα required for nuclear receptor interaction, deletion mutants of RXRα were investigated (FIG. 5a) for their ability to upshift TRα and RARγ (FIGS.

Figure 5B:
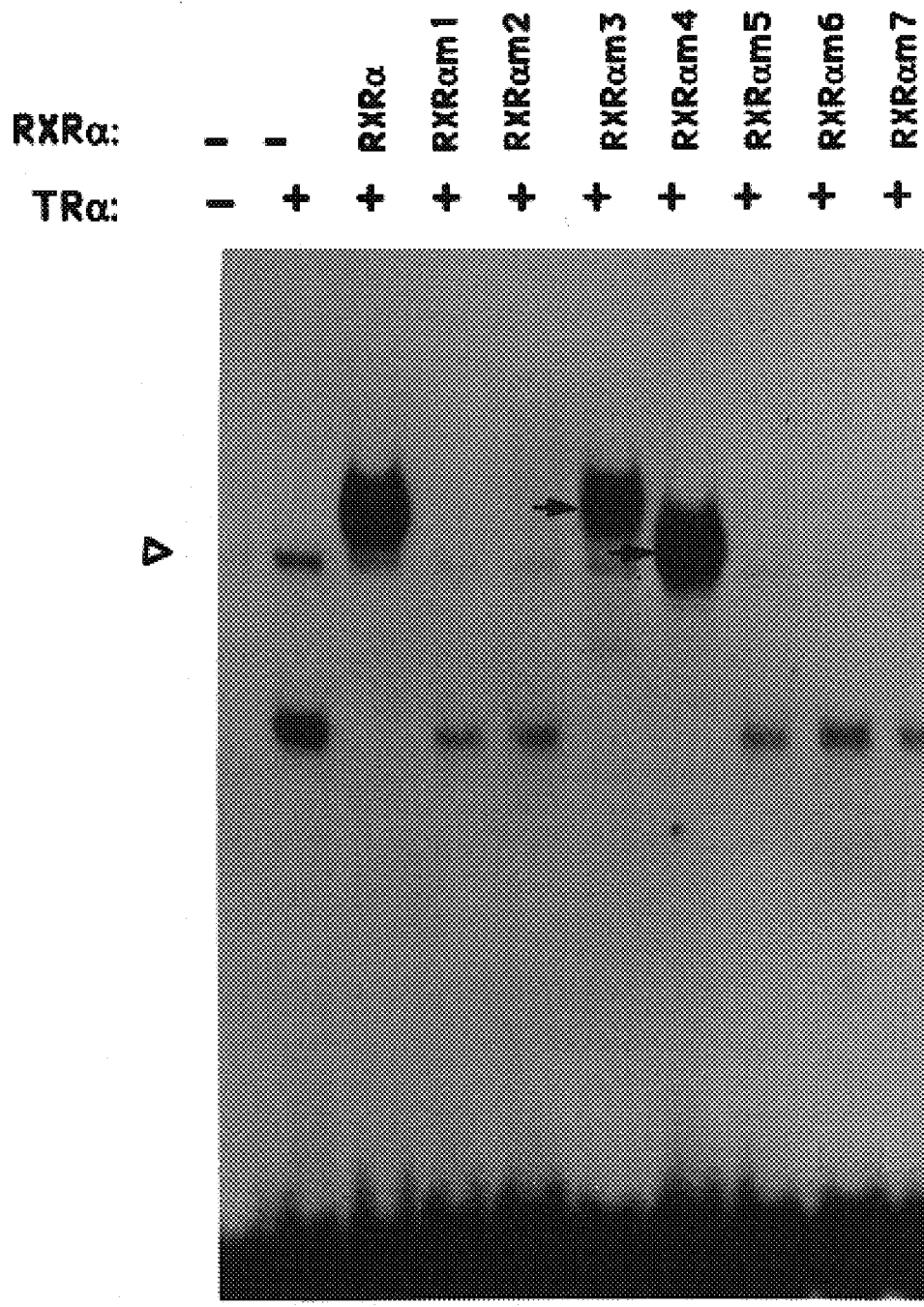
Figure 5C:
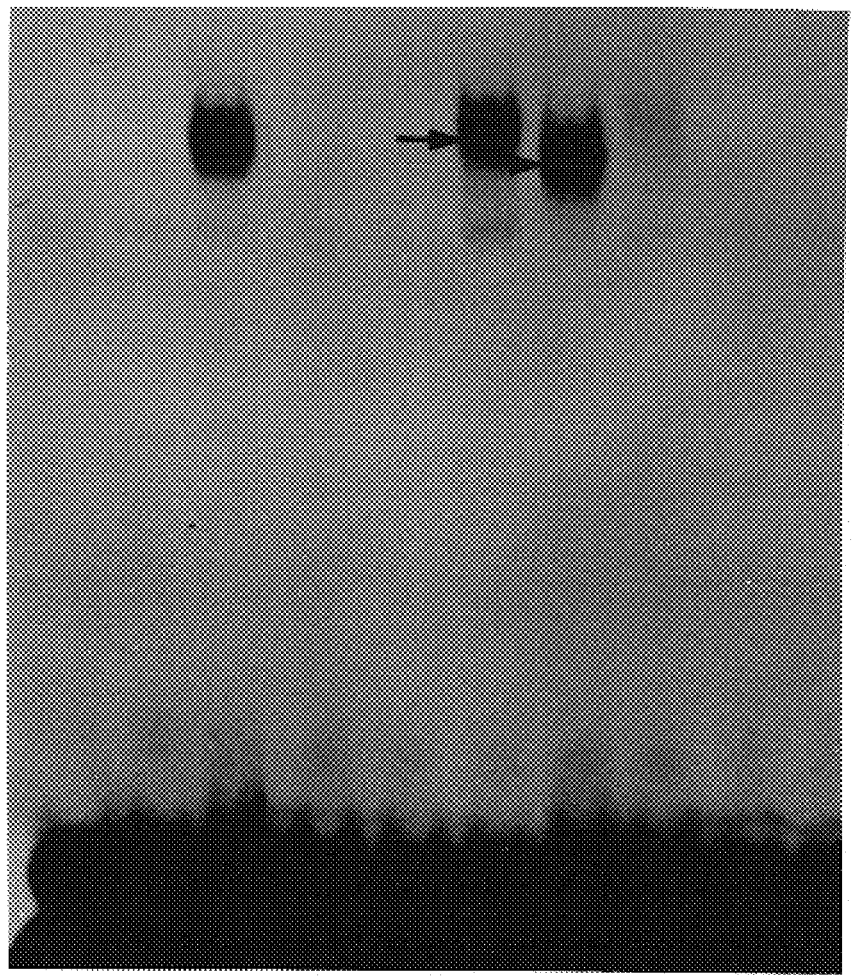

5b,5c). Deletion of 60 (RXRαm1) or 75 (RXRαm2) amino acids from the RXRα carboxyterminus abolished enhancement and upshift of the TRα band while deletion of 28 (RXRαm3) or 61 (RXRαm4) amino acids from the amino terminus did not visibly affect interaction with TRα, as analyzed by the gel retardation assay (FIG. 5b). However, a comparison of the complexes observed with RXRαm3 and RXRαm4 (indicated by arrows) clearly indicates that the size of the RXR protein determines migration of the complex. The smaller protein RXRαm4 forms a faster migrating complex than the larger protein (RXRαm3). These data therefore provide direct evidence that RXRα participates in the complex. In addition, we observed that the carboxyterminal but not the aminoterminal end of RXRα is required for interaction with TRα. Interestingly, an internal deletion that spanned the hinge region and the aminoterminal half of the ligand binding domain (RXRαm7) also abolished interaction with TRα (FIG. 5b). Thus both TRs as well as RXRα require the carboxyterminal domain for heterodimer formation. In addition, however, a truncated RXRα form (RXRαm5) in which the aminoterminal 198 amino acids were deleted (including the DNA binding domain) also failed to form a complex with TRα. A second mutant lacking the DNA binding domain, (RXRαm6), was also unable to upshift TRα. The absence of a complex and the fact that TRα-DNA binding was not inhibited, suggest that portions of the DNA binding region of RXRα are required for interaction with TRα. When we replaced TRα with RARγ identical results were obtained with the RXRα mutants (FIG. 5c). In this experiment, RXRαm4 also forms a complex with RARγ which migrates faster than the complex formed by RXRαm3 and RARγ, as indicated by arrows. Similar results were also obtained when TRβ, RARα and RARβ were used (data not shown). These data thus support the hypothesis that interaction of RXRα with TRs and RARs is mediated by the same structural determinants.

RXRα enhances gene activation by RARs

Figure 6A:
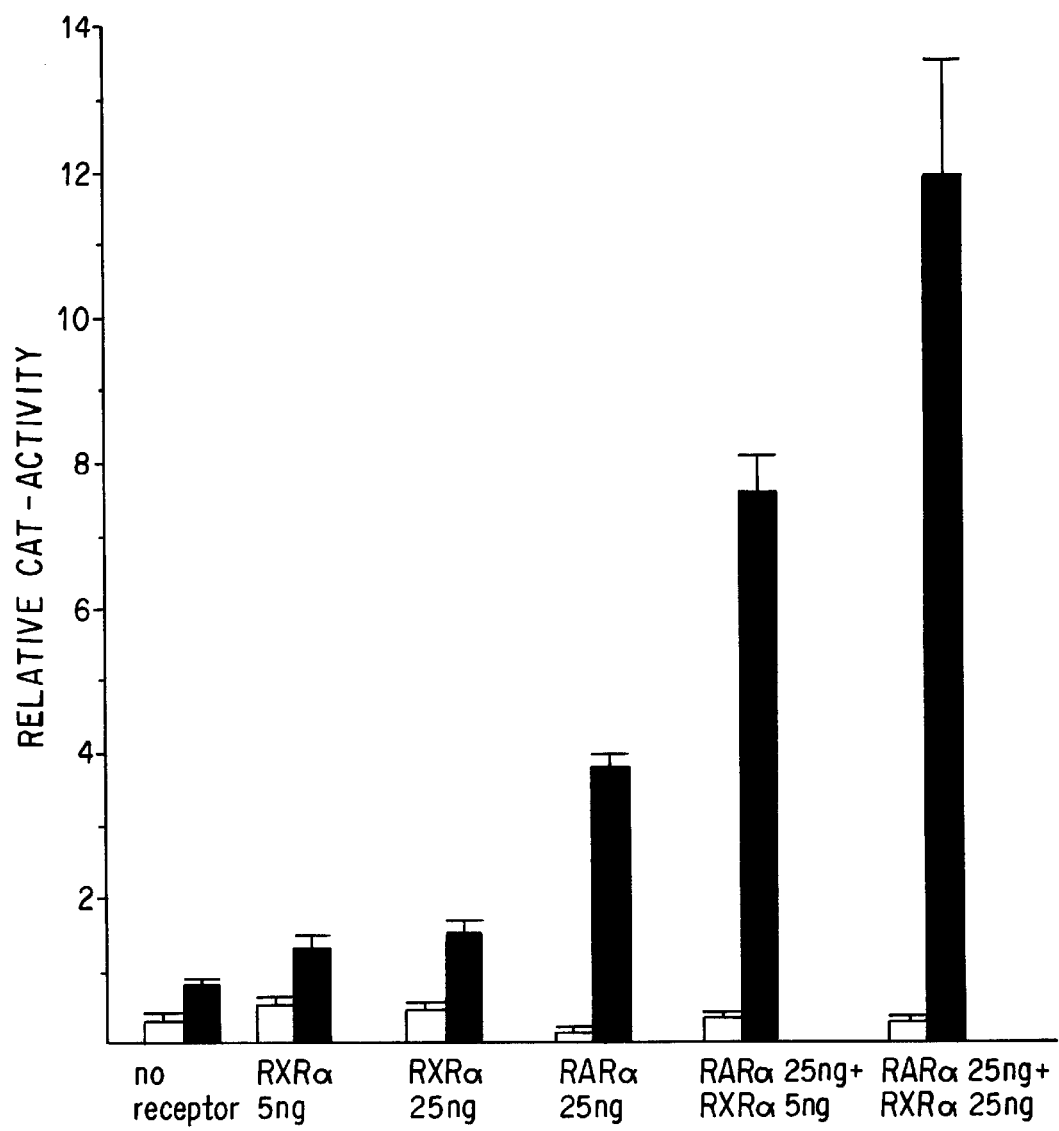
Figure 6B:
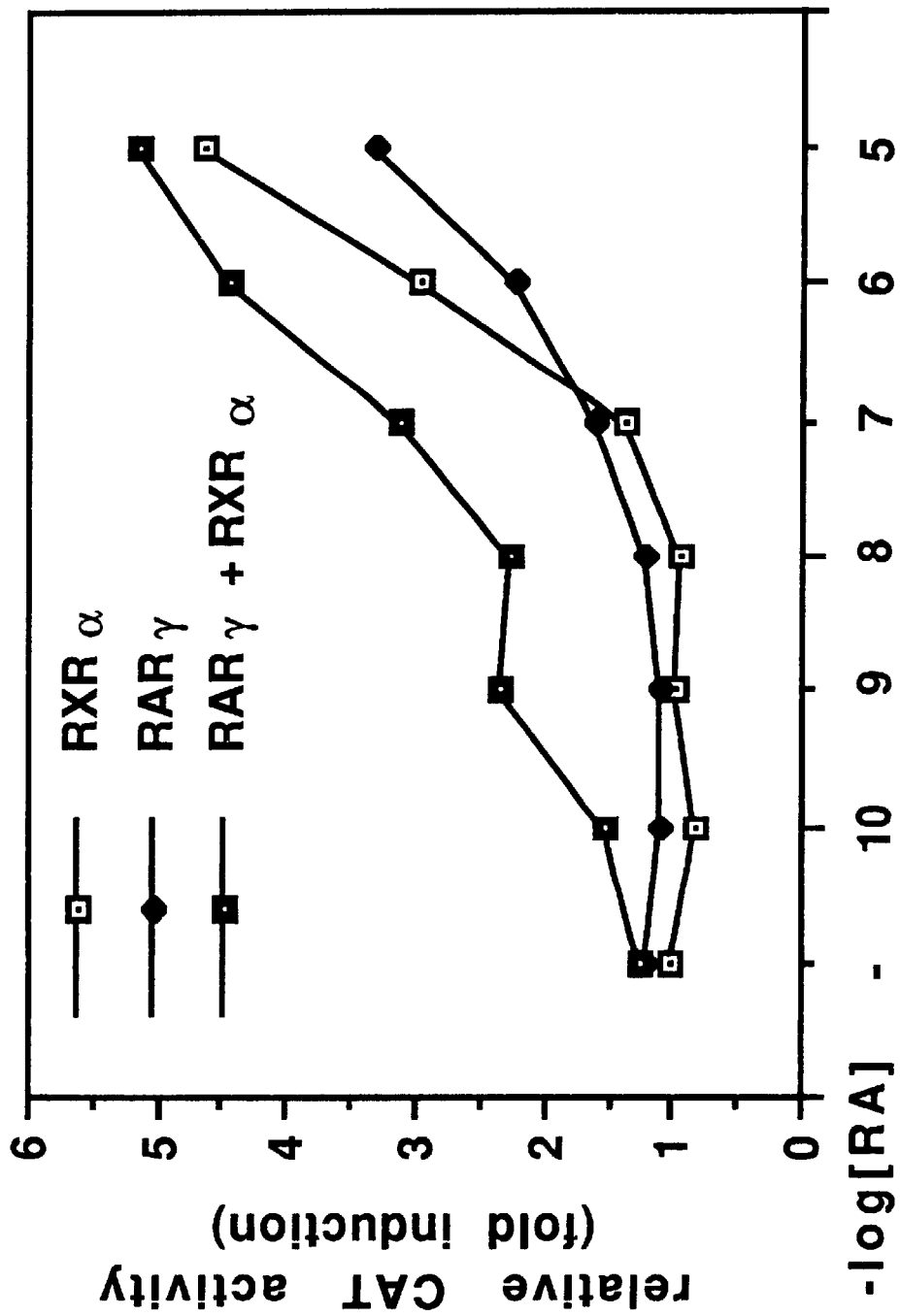

The ability of RXRα to enhance RAR and TR DNA binding could also allow enhancement of transcriptional activation of these receptors on the TRE, a known RA response element (Graupner et al., 1989; Umesono et al., 1988). When low concentrations of RXRα expression vector were cotransfected with RARα and the TRE$_2$-tk-CAT reporter construct, a strong enhancement of the RARα activity was observed (FIG. 6a). Most interestingly, this strong enhancing activity by RXRα was seen at RA concentrations ($10^{-7}$ M) at which RXRα by itself was only slightly activated (FIG. 6b). The increased activation of the reporter gene in the presence of both retinoid receptors is clearly more than additive at certain receptor concentrations as shown. For instance, when 25 ng of RARα and 25 ng of RXRα expression vectors were used, a strong synergistic effect was observed. A very similar enhancing effect was also observed with RARγ (FIG. 6b). In this study, we analyzed the effect of RXRα on RARγ activity under several RA concentrations using the TRE-tk-CAT construct as reporter. At the concentrations used, neither RXRα by itself nor RARγ by itself could elicit any significant transcriptional response at RA concentrations between $10^{-9}$ M and $10^{-7}$ M (FIG. 6b). However, when they were transfected together, a synergistic effect (2 to 4 fold induction) was observed over this RA concentration range. Thus, the ability of RXRα to enhance RAR DNA binding in vitro correlates with an enhanced transcriptional activation capacity of RXRα-RAR complexes in vivo.

Dual ligand requirements of the TRα/RXRα complex

The above experiment did not determine whether RXRα itself requires ligand binding to boost transcriptional activation with RARα or RARγ. When we cotransfected RXRα with TRα, we also observed synergism between both receptors on TRE-tk-CAT reporter constructs (FIG. 7). Some synergism was observed when only thyroid hormone (T$_3$) was added, while optimal synergism required the presence of both ligands, T$_3$ and RA. Remarkably, only low amounts of RXRα as well as TRα were required to observe a strong activation of the reporter genes.

Figure 7A:
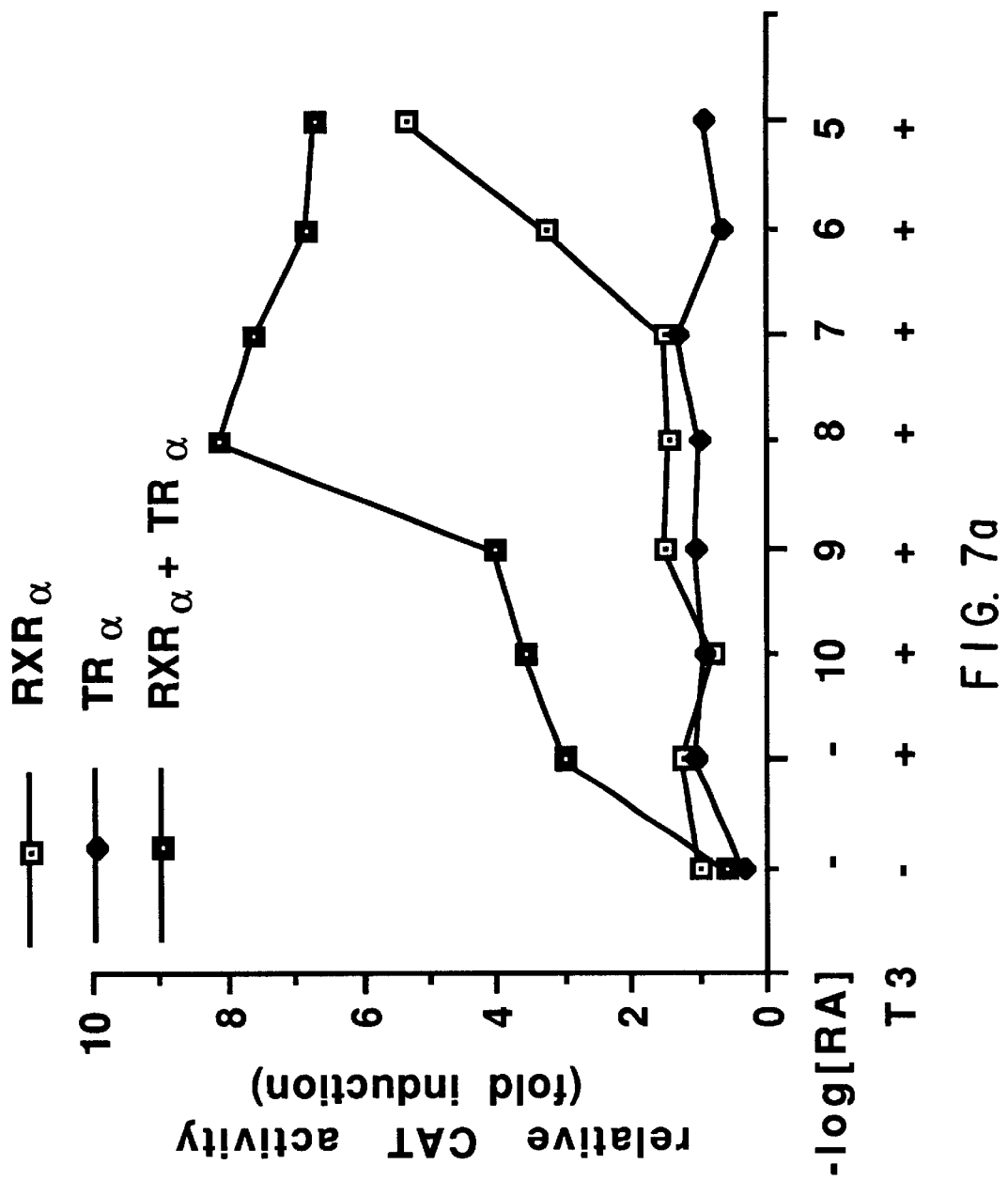
Figure 7B:
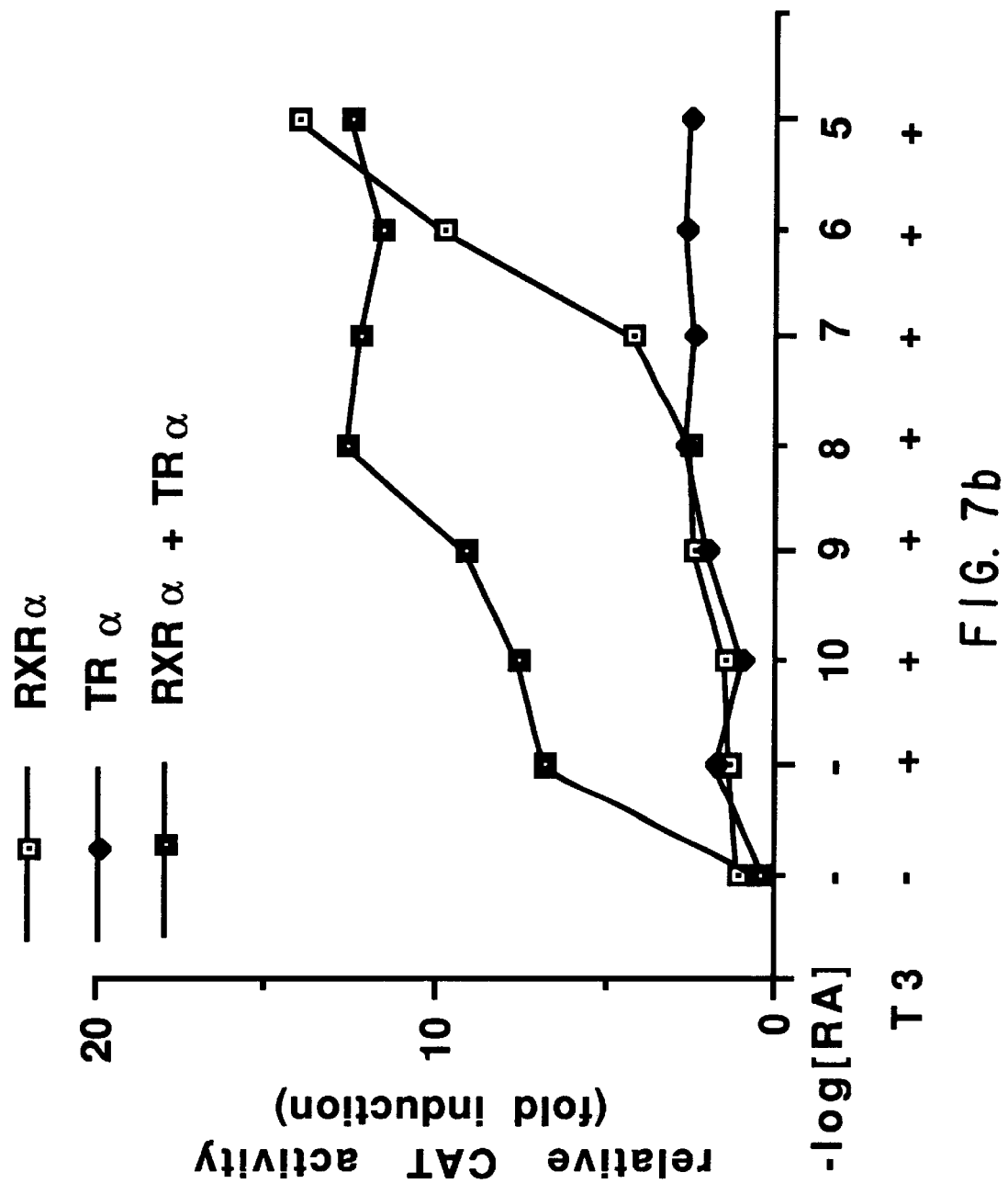

To examine in detail the ligand requirements for the putative RXRα/TRα complex, we compared the RA concentrations required to activate RXRα alone and in combination with TRα. RXRα expression vector alone or together with TRα expression vector were cotransfected into CV-1 cells with reporter constructs that contain either a single (TRE-tk-CAT) or double (TRE$_2$-tk-CAT) response element. Cells were grown in the presence of a constant amount of T$_3$ ($10^{-7}$ M) and various amounts of RA ($10^{-10}$ to $10^{-5}$ M). We observed a dramatic shift of the RA responsiveness of RXRα in the presence of TRα. In cases of both the single TRE and the double TRE reporter, the RXRα sensitivity to RA appeared to be increased by at least 2 orders of magnitude (FIGS. 7a,7b). This enhanced ligand sensitivity is not due to the activation of endogenous RARs by TRα since no effect of CAT activity was observed when TRα was transfected alone (FIGS. 7a,7b) consistent with previous observations (Graupner et al., 1989). TRα alone at this low concentration did not induce the reporter gene to a high degree in the presence of T$_3$, although an approximately 10 fold induction was observed (this is difficult to see on the scale used in FIG. 7). Thus, while RXRα boosts DNA binding and transcriptional activation of other receptors, by forming a complex with TRα, its own ligand affinity is also dramatically increased in the heterodimer complex. Our observation that RXRα exerts its effect on RARα and RARγ transcriptional activity in the presence of less than $10^{-7}$ M RA, suggests that complex formation between RXRα and RARα or RARγ also boosts the ligand sensitivity of RXRα and that RA may be a natural ligand for RXRα.

Heterodimer formation occurs in the absence of DNA

An important question is whether RXRα can form heterodimers with the other receptors in solution or whether the heterodimeric complexes are only formed in the presence of specific DNA sequences. The ability of RXRα to interact with other receptors in the absence of DNA could be expected to largely enhance the efficacy of RXRα as a regulator of heterologous receptor activity. To investigate interaction between RXRα and TR or RAR in the absence of DNA, we took advantage of a unique affinity column containing glutathione coupled to sepharose to which bacterially produced receptor-glutathione transferase fusion protein binds specifically and can be eluted with free glutathione (Smith and Johnson, 1988). TRα or RARγcDNA were cloned into the prokaryotic expression vector pGEX-2T, and expressed as TRα- or RARγ-glutathione transferase fusion proteins in bacteria. The fusion proteins were able to interact with in vitro synthesized RXRα as determined by gel retardation (data not shown). We used bacterially produced TRα- or RARγ-glutathione transferase bound to the affinity resin and mixed this with in vitro synthesized $^{35}$S labelled receptors. After extensive washing, labelled RXRα could be specifically eluted with glutathione from a column that contained bound TRα or RARγ fusion protein, but RXRα was not retained on a column that contained only bound glutathione transferase (FIG. 8). Labelled ER was not retained on by the TRα or RARγ fusion proteins, while the mutant RXRαm4 that lacked 61 amino acids at the amino terminus and was able to upshift TRα and RARγ, was retained.

Figure 8B:
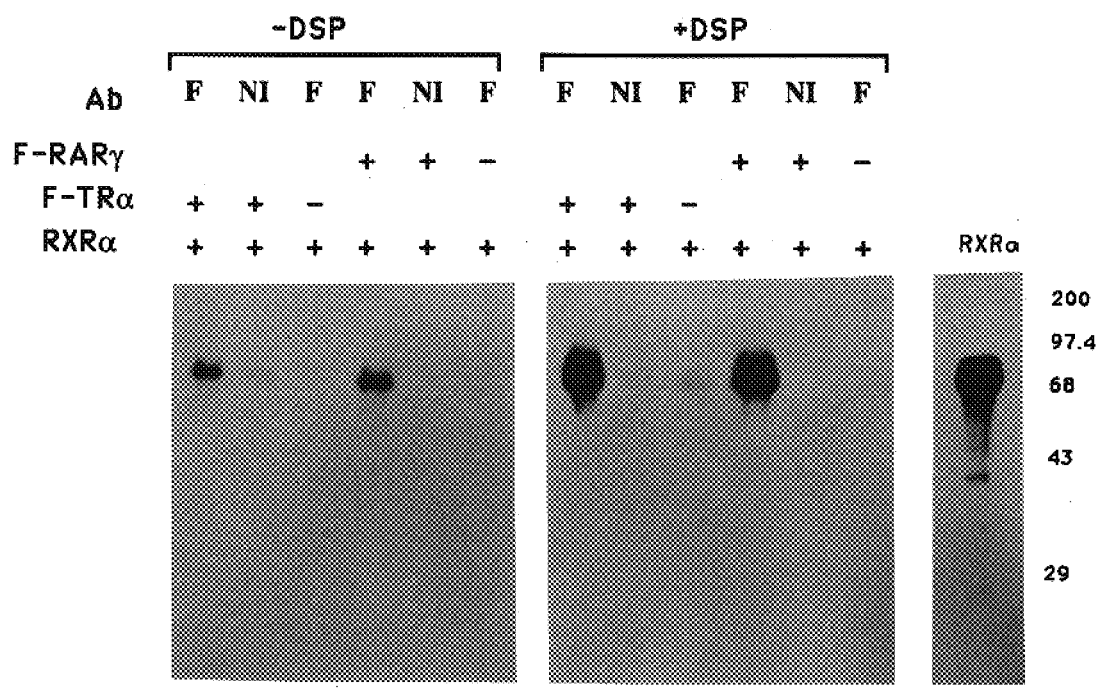

To further document the physical interaction between RXRα and TR or RAR, we incubated labelled RXRα protein, produced by cell-free translation, with or without bacterially produced FLAG-TRα or FLAG-RARγ proteins. Anti-FLAG antibody was used to examine whether RXRα could be precipitated together with FLAG-TRα or FLAG-RARγ. As shown in FIG. 8b, precipitation of FLAG-TRα or FLAG-RARγ resulted in a significant coprecipitation of labelled RXRα protein. The coprecipitation occurred even in the absence of cross-linker while it was largely enhanced when cross-linker (DSP) was used. The coprecipitation is specific since no significant amount of labelled RXRα was precipitated when preimmune serum was used or when RXRα was incubated with nonspecific control protein together with the anti-FLAG antibody. The observation that RXRα could be coprecipitated in the absence of cross-linker and the results obtained with the affinity column strongly suggest that RXRα forms a stable complex with either TR or RAR in solution, and supports our interpretation of the gel retardation results shown in FIG. 2.

Discussion

Heterodimer formation between RXRα and TRS or RARs

Several lines of evidence are provided here for the direct interaction between RXRα and TRs or RARs, which result in the formation of heterodimers which exhibit strong DNA binding to a number of T3/RA dimeric response elements. First, when RXRα was mixed with TRα, TRβ, RARα, RARβ or RARγ, a prominent slow migrating complex was formed which migrated at different positions depending on whether TR or RAR was used (FIG. 1a). Second, using antibodies against RXRα, TR and RAR, we demonstrate that the binding of these slow migrating complexes can be dramatically altered by these antibodies (FIG. 2). Third, RXRα mutational analysis shows that the migration of these complexes depended on the size of the RXRα protein (FIG. 5). Finally, a study using affinity column chromatography and immuno-coprecipitation results demonstrate that RXRα can interact with TR and RAR in the absence of DNA (FIG. 8).

Figure 1C:
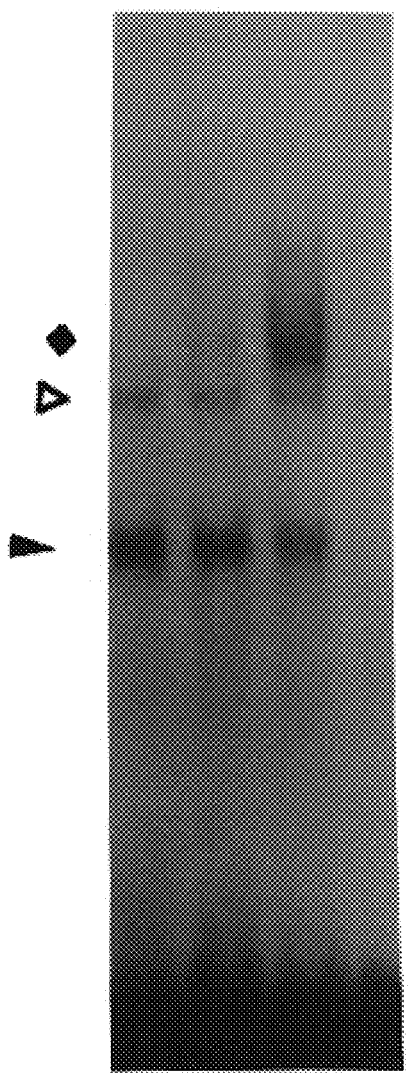
Figure 1D:
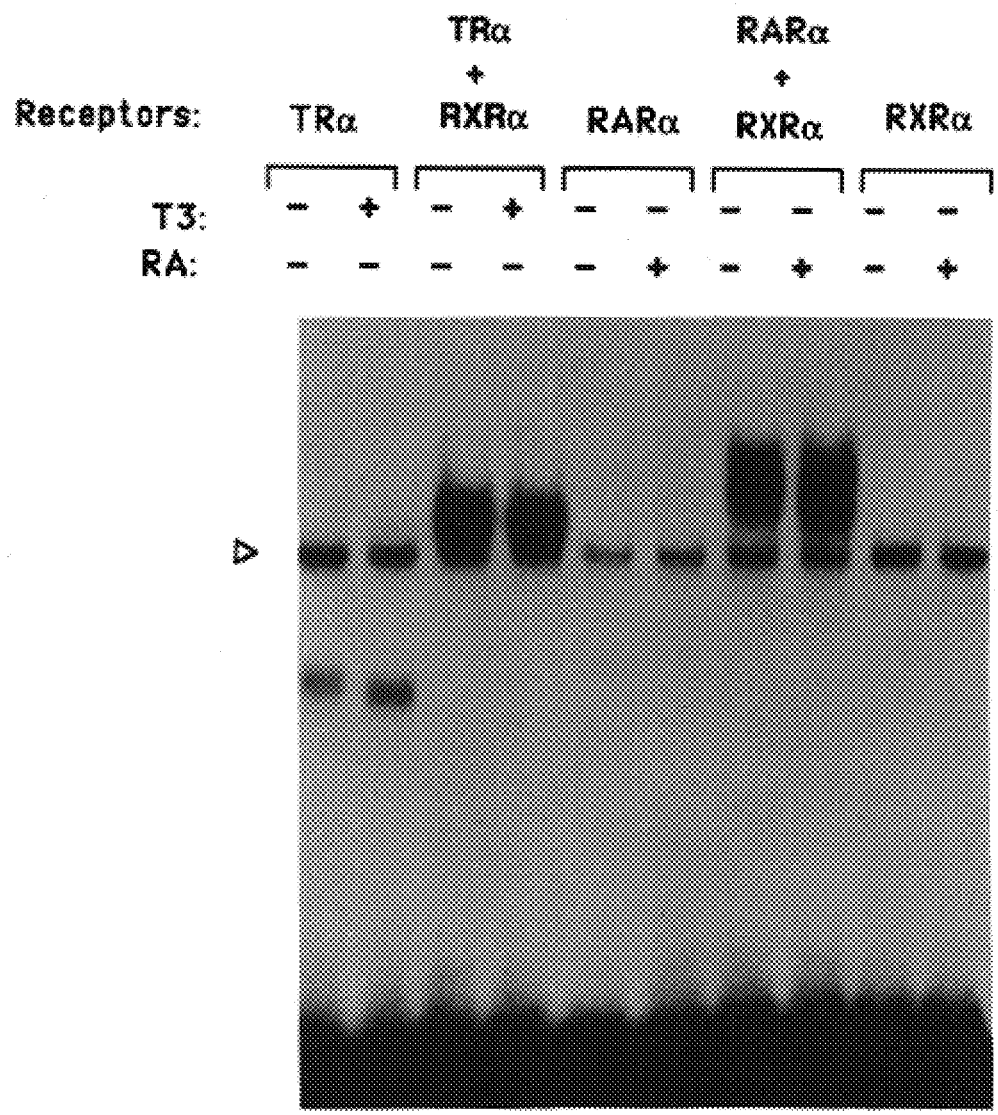

The enhancement of DNA binding and the characteristic upshift observed for all receptors in the presence of RXRα are very similar to the enhanced DNA binding and upshifts of TRα observed in the presence of nuclear extract from several cell lines (FIG. 1c; Zhang et al., 1991a). In addition, all TRα mutants investigated behave virtually identical with RXRα and nuclear extract protein (FIG. 4; Zhang et al., 1991a). It is therefore quite possible that RXRα is identical or closely related to the cellular protein previously described (Lazar and Berrodin, 1990; Murray and Towle, 1989; Burnside et al., 1990). According to its enhancing effects on TR DNA binding, the nuclear protein or proteins that enhance TR DNA binding have been termed TR auxiliary proteins—TRAP (reviewed by Rosen et al., 1991). However, if these proteins are identical with RXRα or a related isoform, this nomenclature is insufficient to describe their function. RXRα, as an example of this new receptor subclass, can not dimerize by itself efficiently but can interact with TRs or RARs to form heterodimers with strong DNA binding activity.

TR and RAR as well as RXRα require regions near the carboxyterminal end for interaction (FIG. 4 and FIG. 5). Interestingly, these regions are also required for TR interaction with cJun, a component of the transcription factor AP-1 that has recently been shown by us to regulate TR and RAR activities (Zhang et al., 1991c; Yang-Yen et al., 1991). Thus, this carboxyterminal region may be viewed as a domain that can interfere with other active protein regions in possibly both cis and trans locations. The ligand binding domain of TRs and RARs was shown to possess 9 heptad repeats of hydrophobic amino acids which are structurally similar to the Leucine-Zipper dimerization domain (Forman et al., 1990). These Leucine-Zipper like motifs are thought to mediate the receptor dimerization activity by a coiled-coil a helix in which a hydrophobic surface along one side of the helix could act as a dimerization interface. Similar heptad repeats are also present in the ligand binding domain of RXRα. The requirement of the ligand binding domain of both RXRα and TR or RAR for heterodimer formation implicates these Leucine-Zipper like motifs in the direct interaction between both receptors. However, RXRα may possess some other special structural features which are not present in TR or RAR since we could not observe clear interaction between TR and RAR when they were mixed together and were assayed under the same conditions (FIG. 1a). These special structural features may not allow RXRα homodimer formation, but allow RXRα to efficiently interact with TR and RAR. A detailed mutational analysis of RXRα receptor protein is therefore important in order to understand the mechanism of interaction between RXRα and TR or RAR. While the heptad repeats in the ligand binding domain of RAR, TR and RXRα may effectively interact with each other, and thereby allow receptor contact, at the same time the interaction may be extended through the dimerization domain embedded in the DNA binding region of nuclear receptors (Zhang et al., 1991a; Hard et al.,1990; Luisi et al., 1991; Schwabe et al.,1990). This is supported by our observation that the DNA binding domain of RXRα is also important for efficient interaction with TR or RAR (FIG. 5).

TRs and RARs are important mediators of cellular development and differentiation processes. The observation that RXRα can interact with TRs and RARs in the absence of DNA (FIG. 8) and the fact that the heterodimer can bind to a number of T3/RA specific response elements (FIG. 3) point to the profound role of RXRα in regulating these cellular processes. Although interaction between RXRα and TR or RAR occurs in solution, the outcome of this interaction may depend on the sequence of the response element in particular genes. In other words, the specificity and the extent of transcriptional regulation, either positively or negatively, by receptor interactions may be largely determined by the nature of the response elements and the receptors (and their concentrations) with which RXRα interacts.

Transcriptional activity of RXRα

Synergistic transcriptional activity of RAR and TR on the palindromic TRE was observed when they were cotransfected with RXRα (FIG. 6 and FIG. 7). These in vivo observations correlate very well with the strong DNA binding of heterodimers formed between RXRα and TR or RXRα and RAR. Interestingly, considerable enhancing activity of RXRα is observed in the absence of RA while optimal enhancement occurs already at low RA concentrations (less than $10^{-7}$ M), whereas higher RA concentrations are required to activate RXRα alone (more than $10^{-6}$ M; FIG.6, FIG.7; Mangelsdorf et al., 1990). Thus, while RXRα boosts very efficiently the activity of TRs and RARs in terms of DNA binding and transcriptional activation, its own ligand responsiveness is also boosted by the heterodimerization, i.e. mutual enhancement is occurring. This is most likely one of the major roles of RXR. We like to call this novel activity a "booster receptor" (B-receptor), in contrast to activator receptors (A-receptors). In addition to its enhancer activity, RXR forms a complex with TRα (and TRβ, data not shown) that appears to require two distinct hormones for full activation. This novel type of receptor complex allows direct cross-talk between two different hormonal signals at the receptor level. The palindromic TRE analyzed here is derived from the growth hormone (GH) TRE. Two years ago, Bedo et al. (1989) reported that the GH gene can be induced by RA and that the presence of $T_3$ increases the effectivity of RA by close to 3 orders of magnitude (from $10^{-6}$ M to $10^{-9}$ M for optimal induction). This type of in vivo observation is very similar to ours, where $10^{-5}$ M RA are required for RXRs activation while $10^{-8}$ M is sufficient for activation of RXRα in the presence of TRα and $T_3$. A comparable synergistic effect has recently also been reported for the induction of granulocyte differentiation in leukemic cells including HL60 (Ballerini et al., 1991). Because low concentrations of RXRα are sufficient for boosting RARα and TRα activity, an extremely sensitive regulatory mechanism is created that can respond very efficiently to small changes in the concentrations of individual components. Our data suggest that, contrary to earlier suggestions (Mangelsdorf et al., 1990), RA is an important natural ligand for RXRα; whether other natural retinoids exist that effectively activate RXRα homodimers at physiological concentrations remains to be determined.

At present it appears that more than one RXR subtype exists (RXRα and RXRβ) that may have distinct booster specificities. Even the same RXR subtype may show considerable selectivity depending on the response element (FIG. 3), interacting receptor and receptor concentration (FIG. 6a). We have provided evidence here that the booster capacity for RXRα towards TRα is much higher than towards RARγ (FIG. 6 and FIG. 7), and effective over a wider receptor concentration range as well (data not shown).

The subfamily of B-receptors may also include a substantial number of orphan receptors for which no specific ligands could be detected so far or other receptors that require very high ligand concentrations for efficient activation. Since RXRs appears to be encoded by more than one gene (Mangelsdorf et al., 1990; Hamada et al., 1989), RXRβ whose DNA and ligand binding domains are almost identical to those of RXRα is an equally good candidate. In general, the mechanisms of heterodimer formation are widely used by transcription factors, the most well known examples being AP-1 (reviewed by Karin, 1990) and the more recently described myc-max heterodimeric (Blackwood and Eisenman, 1991). Because of the obvious advantage of heterodimeric and booster receptors in many systems, our studies presented here may be the tip of the iceberg of a large field of receptor action not yet explored.

REFERENCES

Ballerini P., Lenoble, M., Balitrand, N., Schaison, G., Najean, Y., and Chomienne, C. (1991). Stimulatory effect of thyroid hormone on RA-induced granulocytic differentiation in leukemic cells. Leukemia 5, 383–385.

Baniahmad, A., Steiner, C., Kohne, A. C., and Renkawitz, R. (1990). Modular structure of a chicken lysozyme silencer: involvement of an unusual thyroid hormone receptor binding site. Cell 61, 505–514.

Bedo, G., Santisteban, P., and Aranda, A. (1989). Retinoic acid regulates growth hormone gene expression. Nature 339, 231–233.

Benbrook, D., and Pfahl, M. (1987). A novel thyroid hormone receptor encoded by a cDNA clone from a human testis library. Science 238, 788–791.

Benbrook, D., Lernhardt, E., and Pfahl, M. (1988). A new retinoic acid receptor identified from a hepatocellular carcinoma. Nature 333, 669–672.

Blackwood, E. M., and Eisenman, R. N. (1991). Max: a helix-loop-helix zipper protein that forms a sequence-specific DNA-binding complex with myc. Nature 251, 1211–1217.

Brent, G. A., Dunn, M. K., Harney, J. W., Gulick, T., Larsen, P. R., and Moore, D. D. (1989). Thyroid hormone aporeceptor represses $T_3$-inducible promoters and blocks activity of the retinoic acid receptors. New Biol 1,329–336.

Burnside, J., Darling, D. S., and Chin, W. W. (1990). A nuclear factor that enhances binding of thyroid hormone receptors to thyroid response elements. J Biol Chem 265, 2500–2504.

Damm, K., Thompson, C. C., and Evans, R. M. (1989). Protein encoded by v-erbA functions as a thyroid-hormone receptor antagonist. Nature 339, 593–597.

de The, H., Vivanco-Ruiz, M. M., Tiollais, P., Stunnenberg, M., and Dejean, A. (1990). Identification of a retinoic acid response element in the retinoic acid receptor B gene. Nature 343, 177–180.

Evans, R. M. (1988). The steroid and thyroid hormone receptor family. Science 240, 889–895.

Forman, B. M., and Samuels, H. H. (1990). Interactions among a subfamily of nuclear hormone receptors: the regulatory zipper model. Mol. Endocrinol. 4, 1293–1301.

Forman, B. M., and Samuels, H. H. (1991). p EXPRESS: a family of novel expression vectors containing a single transcription unit that is active in vitro, in prokaryotes and in eukaryotes. (in press).

Forman, B. M., Yang, C-r., Au, M., Casanova, J., Ghysdael, J., and Samuels, H. H. (1989). A domain containing leucine-zipper-like motifs between the thyroid hormone and retinoic acid receptors. Mol Endocrinol 3, 1610–1626.

Giguere, V., Ong, E. S., Seigi, P., and Evans, R. M. (1987). Identification of a receptor for the morphogen retinoic acid. Nature, 330, 624–629.

Glass, C. K., Holloway, J. M., Devary, O. V., and Rosenfeld, M. G. (1988). The thyroid hormone receptor binds with opposite transcriptional effects to a common sequence motif in thyroid hormone and estrogen response elements. Cell 54, 313–323.

Glass, C. K., Devary, O. V., and Rosenfeld, M. G. (1990). Multiple cell type-specific proteins differentially regulate target sequence recognition by the α retinoic acid receptor Cell 63, 729–738.

Graupner, G., Wills, K. N., Tzukerman, M., Zhang, X-K., and Pfahl, M. (1989). Dual regulatory role for thyroid-hormone receptors allows control of retinoic-acid receptor activity. Nature 340, 653–656.

Graupner, G., Zhang X-k., Tzukerman, M., Wills, K., Hermann, T., and Pfahl, M. (1991). Thyroid hormone receptors repress estrogen receptor activation of a TRE. Mol. Endocrinol. 5, 365–372.

Green, S., and Chambon, P. (1988). Nuclear receptors enhance our understanding of transcription regulation. Trends Genet 4, 309–314.

Hamada, K., Gleason, S. L., Levi, B-Z., Hirschfeld, S., Appella, E., and Ozato, K. (1989). H-2RIIBP, a member of the nuclear hormone receptor superfamily that binds to both the regulatory element of major histocompatibility class I genes and the estrogen response element. Proc. Natl. Acad. Sci., USA 86, 8289–8293.

Härd, T., Kellenbach, E., Boelens, R., Maler, B. A., Dahlman, K., Freeman, L. P., Carlstedt-Duke, J., Yamamoto, K. R., Gustafsson, J-Å., and Kaptein, R. (1990). Solution structure of the glucocorticoid receptor DNA-binding domain. Science 249, 157–160.

Hermann, T., Zhang, X-k., Tzukerman, M., Wills, K. N., Graupner, G., and Pfahl, M. (1991). Regulatory functions of a non-ligand binding thyroid hormone receptor isoform. Cell Regulation 2, 565–574.

Hodin, R. A., Lazar, M. A., Wintman, B. I., Darling, D. S., Koenig, R. J., Larsen, P. R., Moore, D., and Chin, W. W. (1989). Identification of a thyroid hormone receptor that is pituitary-specific. Science 244, 76–78.

Hoffmann, B., Lehmann, J. M., Zhang, X-k., Hermann, T., Husmann, M., Graupner, G., and Pfahl, M. (1990). A retinoic acid receptor-specific element controls the retinoic acid receptor-B promoter. Mol. Endocrinol. 4, 1727–1736.

Hopp, T. P., Prickett, K. S., Price, V. L., Libby, R. T., March C. J., Cerretti, D. P., Urdal, D. L., and Conlon, P. J.(1988). A short polypeptide marker sequence useful for recombinant protein identification and purification. Bio-Technology 6, 1204–1210.

Husmann, M., Lehmann, J., Hoffmann, B., Hermann, T., Tzukerman, M., and Pfahl, M. (1991). Antagonism between retinoic acid receptors. Mol. Cell. Biol. 11, 4097–4103.

Jansson, M., Philipson, L., and Vennstrom, B. (1983). Isolation and characterization of multiple human genes homologous to the oncogenes of avian erythroblastosis virus. EMBO J 2, 561–565.

Karin, M. (1990). The AP-1 complex and its role in transcriptional control by protein kinase C. Molecular Aspects of Cellular Regulation 6, 143–161.

Klein-Hitpass, L., Schorpp, M., Wagner, U., and Ryffel, G. U. (1986). An estrogen-responsive element derived from the 5' flanking region of the Xenopus vitellogenin A2 functions in transfected human cells. Cell 46, 1053–1061.

Koenig, R. J., Lazar, M. A., Hodin, R. A., Brent, G. A., Larsen. P. R., Chin, W. W., and Moore, D. D. (1989). Inhibition of thyroid hormone action by a non-hormone binding c-erbA protein generated by alternative mRNA splicing. Nature 337, 659–660.

Krust, A., Kastner, P. H., Petkovich, M., Zelent, A., and Chambon, P. (1989). A third human retinoic acid receptor, hRAR-γ. Proc. Natl. Acad. Sci. USA 86, 5310–5314.

Lazar, M. A., and Berrodin, T. J. (1990). Thyroid hormone receptors form distinct nuclear protein-dependent and independent complexes with a thyroid hormone response element. Mol Endocrinol 4, 1627–1635.

Lazar, M. A., Hodin, R. A., and Chin, W. W. (1989). Human carboxyl-terminal variant of a-type c-erbA inhibits transactivation by thyroid hormone receptors without binding thyroid hormone. Proc Natl Acad Sci USA 86, 7771–7774.

Lehmann, J. M., Hoffmann, B., and Pfahl, M. (1991a). Genomic organization of the retinoic acid receptor gamma gene. Nucleic Acids Research 19, 573–578.

Leroy, P., Krust, A., Zelent, A., Mendelsohn, C., Garnier, J-M., Kastner, P., Dierich, A., and Chambon, P. (1991). Multiple isoforms of the mouse retinoic acid receptor a are generated by alternative splicing and differential induction by retinoic acid. EMBO Journal 10, 59–69.

Luisi, B. F., Xu, W. X., Otwinowski, Z., Freedman, L. P., Yamamoto, K. R., and Sigler, P. B. Crystallographic analysis of the interaction of glucocorticoid receptor with DNA. Nature 352, 497–505.

Mangelsdorf, D. J., Ong, E. S., Dyck, J. A., and Evans, R. M. (1990). Nuclear receptor that identifies a novel retinoic acid response pathway. Nature 345, 224–229.

Millan, J. L. (1986). Molecular cloning and sequence analysis of human placental alkaline phosphatase. J. Biol. Chem. 261, 3112–3115.

Mitsuhashi, T., Tennyson, G. E., and Nikodem, V. M. (1988). Alternative splicing generates messages encoding rat cerbA proteins that do not bind thyroid hormone. Proc Natl Acad Sci USA 85, 5804–5808.

Murray, M. B., and Towle, H. C. (1989). Identification of nuclear factors that enhance binding of the thyroid hormone receptor to a thyroid hormone response element. Mol Endocrinol 3, 1434–1442.

Naär, A. M., Boutin, J-M., Lipkin, S. M., Yu, V. C., Holloway, J. M., Glass, C. K., and Rosenfeld, M. G. (1991). The orientation and spacing of core DNA-binding motifs dictate selective transcriptional responses to three nuclear receptors. Cell 65,1267–1279.

Nakai, A., Sakurai, A., Bell, G. I., and DeGroot, L. J. (1988a). Characterization of a third human thyroid hormone receptor co-expressed with other thyroid hormone receptors in several tissues. Mol Endo 2, 1087–1092.

Petkovich, M., Brand, N. J., Krust, A., and Chambon, P. (1987). A human retinoic acid receptor which belongs to the family of nuclear receptors. Nature 330, 444–540.

Pfahl, M. and Benbrook, D. (1987). Nucleotide sequence of CDNA encoding a novel thyroid hormone receptor. Nucl. Acids. Res. 15, 9613.

Pfahl, M., Tzukerman, M., Zhang, X-k., Lehmann, J. M., Hermann, T., Wills, K. N., and Graupner, G. (1990). Rapid procedures for nuclear retinoic acid receptor cloning and their analysis. Methods Enzymol. 189, 256–270.

Rosen, E. D., O'Donnell, A. L., and Koenig, R. J. (1991). Protein-protein interactions involving erbA superfamily receptors: through the TRAP door. Mol Cell Endocrinol 78, C83–C88.

Sakurai, A., Nakai, A., and DeGroot, L. J. (1989a). Expression of three forms of thyroid hormone receptor in human tissues. Mol Endocrinol 3, 392–399.

Sap, J., Muhoz, A., Damm, K., Goldberg, Y., Ghysdael, J., Leutz, A., Beug, H., and Vennstrom, B. (1986). The c-erbA protein is a high-affinity receptor for thyroid hormone. Nature 324, 635–640.

Schueler, P. A., Schwartz, H. L., Strait, K. A., Mariash, C. N., and Oppenheimer, J. H. (1990). Binding of 3,5,3'-Triiodothryonine ($T_3$) and its analogs to the in vitro translation produces of c-erbA protooncogenes: differences in the affinity of the α- and β-forms for the acetic acid analog and failure of human testis and kidney α-2 products to bind $T_{23}$. Mol. Endocrinol 4, 227–234.

Schwabe, J. W. R., Neuhaus, D., and Rhodes, D. (1990). Solution structure of the DNA-binding domain of the estrogen receptor. Nature 348, 458–461.

Smith, D. B., and Johnson, K. S. (1988). Single-step purification of polypeptides expressed in *Escherichia coli* as fusions with glutathione S-transferase. Gene 67, 3140.

Thompson, C. C., Weinberger, C., Lebo, R., and Evans, R. M. (1987). Identification of a novel thyroid hormone receptor expressed in the mammalian central nervous system. Science 237, 1610–1613.

Umesono, K., Giguere, V., Glass, C. K., Rosenfeld, M. G., and Evans, R. M. (1988). Retinoic acid and thyroid hormone induce gene expression through a common responsive element. Nature 336, 262–265.

Umesono, K., Murakami, K. K., Thompson, C. C., and Evans, R. M. (1991). Direct repeats as selective response elements for the thyroid hormone, retinoic acid, and vitamin $D_3$ receptors. Cell 65, 1255–1266.

Weinberger, C., Thompson, C. C., Ong, E. S., Lebo, R., Gruol, D. J., and Evans, R. M. (1986). The c-erb-A gene encodes a thyroid hormone receptor. Nature 324, 641–646.

Yang-Yen, H. F., Zhang, X-k., Graupner, G., Tzukerman, M., Sakamoto, B., Karin, M., and Pfahl, M. (1991). Antagonism between retinoic acid receptors and AP-1: implications for tumor promotion and inflammation. New Biol. (in press).

Zelent, A., Mendelsohn, C., Kastner, P., Krust, A., Garnier, J-M., Ruffenach, F., Leroy, P., and Chambon, P. (1991). Differentially expressed isoforms of the mouse retinoic acid receptor B are generated by usage of two promoters and alternative splicing. EMBO Journal 10, 71–81.

Zhang, X-k., Tram, P., and Pfahl, M. (1991a) DNA binding and dimerization determinants for TRα and its interaction with a nuclear protein. (accepted for publication Mol. Endocrinol.).

Zhang, X-K., Wills, K. N., Graupner, G., Tzukerman, M., Hermann, T., and Pfahl, N. (1991b). Ligand-binding domain of thyroid hormone receptors modulates DNA binding and determines their bifunctional roles. New Biol 3, 1–14.

Zhang, X-k., Wills, K. N., Hermann, T., Husmann, M., and Pfahl, M. (1991c). A novel pathway for thyroid hormone receptor action through interaction with JUN and FOS oncogene activities. Mol. Cell. Biol. (in press).

---

What is claimed is:

1. A purified heterodimer comprising a retinoid x receptor (RXR) and a hormone receptor.
2. The heterodimer of claim 1, wherein the RXR is RXRα.
3. The heterodimer of claim 1, wherein the hormone receptor is a thyroid hormone receptor.
4. The heterodimer of claim 3, wherein the thyroid hormone receptor is TRα.
5. The heterodimer of claim 1, wherein the hormone receptor is a retinoic acid receptor.
6. The heterodimer of claim 5, wherein the retinoic acid receptor is RARα.
7. The heterodimer of claim 1, further bound to a ligand.
8. The heterodimer of claim 7, wherein the ligand is retinoic acid.
9. The heterodimer of claim 7, wherein the ligand is thyroid hormone.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

CGCAGACATG GACACCAAAC AT                              22

(2) INFORMATION FOR SEQ ID NO:2:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CCTCTCCACC GGCATGTCCT CG                                                  22

(2) INFORMATION FOR SEQ ID NO:3:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

Arg Tyr Lys Asp Asp Asp Asp Lys
1               5

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

TCAGGTCATG ACCTGA                                                         16

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

GATCCTGACC TGAGATCTCA GGTCAG                                              26

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

GATCTCAGGT CA                                                             12

(2) INFORMATION FOR SEQ ID NO:7:

(i) SEQUENCE CHARACTERISTICS:
```

(A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

AGGGTTCAGG CAAAGTTCAC                                              20

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

TCAGGTCACT GTGACCTGA                                               19

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

GATCTCAGGT CATGACCTGA GATC                                         24

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

GATCCTGACC TGAGATCTCA GGTCAGGATC                                   30

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

GATCAGGGTT CAGGCAAAGT TCACGATC                                     28

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: double
        (D) TOPOLOGY: linear

```
            (ii) MOLECULE TYPE: DNA (genomic)

(xi) SEQUENCE DESCRIPTION: SEQ ID NO:12:

GATCTCAGGT CAGATC                                                          16

(2) INFORMATION FOR SEQ ID NO:13:

(i) SEQUENCE CHARACTERISTICS:
           (A) LENGTH: 27 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:13:

GATCTCAGGT CACTGTGACC TGAGATC                                              27

(2) INFORMATION FOR SEQ ID NO:14:

(i) SEQUENCE CHARACTERISTICS:
           (A) LENGTH: 16 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:14:

TCAGGTCATG ACCTGA                                                          16

(2) INFORMATION FOR SEQ ID NO:15:

(i) SEQUENCE CHARACTERISTICS:
           (A) LENGTH: 49 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:15:

GATCCGCGGC CGCCACCATG GATTACAAGG ACGACGACGA TAAGATCTG                      49

(2) INFORMATION FOR SEQ ID NO:16:

(i) SEQUENCE CHARACTERISTICS:
           (A) LENGTH: 49 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:16:

GCGCCGGCGG TGGTACCTAA TGTTCCTGCT GCTGCTATTC TAGACAGCT                      49
```